(12) United States Patent
Smith et al.

(10) Patent No.: US 11,986,647 B2
(45) Date of Patent: May 21, 2024

(54) TREATING AUTOINFLAMMATORY AND MITOCHONDRIAL DISEASES USING AN ALTERNATING ELECTRIC FIELD

(71) Applicant: Novocure GmbH, Root (CH)

(72) Inventors: Stuart Smith, Notts (GB); Lilach Avigdor, Haifa (IL); Tali Voloshin-Sela, Haifa (IL)

(73) Assignee: Novocure GmbH, Root (CH)

( * ) Notice: Subject to any disclaimer, the term of this patent is extended or adjusted under 35 U.S.C. 154(b) by 343 days.

(21) Appl. No.: 17/358,258

(22) Filed: Jun. 25, 2021

(65) Prior Publication Data

US 2021/0379362 A1 Dec. 9, 2021

Related U.S. Application Data

(63) Continuation-in-part of application No. 17/333,509, filed on May 28, 2021, which is a continuation of application No. 16/560,134, filed on Sep. 4, 2019, now Pat. No. 11,020,585.

(60) Provisional application No. 63/045,980, filed on Jun. 30, 2020, provisional application No. 63/045,378, filed on Jun. 29, 2020, provisional application No. 63/045,390, filed on Jun. 29, 2020, provisional application No. 62/728,174, filed on Sep. 7, 2018.

(51) Int. Cl.
*A61N 1/04* (2006.01)
*A61N 1/32* (2006.01)
*A61N 1/36* (2006.01)

(52) U.S. Cl.
CPC ......... *A61N 1/0456* (2013.01); *A61N 1/3616* (2013.01)

(58) Field of Classification Search
CPC .......... A61N 1/32; A61N 1/321; A61N 1/326; A61N 1/36; A61N 1/36002
See application file for complete search history.

(56) References Cited

U.S. PATENT DOCUMENTS

| 6,868,289 B2 | 3/2005 | Palti |
| 7,016,725 B2 | 3/2006 | Palti |
| 7,089,054 B2 | 8/2006 | Palti |

(Continued)

FOREIGN PATENT DOCUMENTS

| WO | 2005115535 A2 | 12/2005 |
| WO | 2006085150 A2 | 8/2006 |
| WO | 2016007653 A2 | 1/2016 |

OTHER PUBLICATIONS

Abeler-Dorner et al., "Butyrophilins: an emerging family of immune regulators," Trends in Immunology, vol. 33, pp. 34-41, 2012.

(Continued)

*Primary Examiner* — Brian T Gedeon
(74) *Attorney, Agent, or Firm* — Potomac Law Group, PLLC

(57) ABSTRACT

Autoinflammatory and mitochondrial disorders can be treated by positioning a plurality of electrodes in or on a subject's body, and applying an AC voltage between the plurality of electrodes so as to impose an alternating electric field through the tissue that is being affected by the autoinflammatory or mitochondrial disease. The frequency and field strength of the alternating electric field are selected such that the alternating electric field inhibits inflammation or mitochondrial disorders in the tissue.

23 Claims, 18 Drawing Sheets

(56) References Cited

U.S. PATENT DOCUMENTS

| | | | |
|---|---|---|---|
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Paiti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Paiti | |
| 9,023,091 B2 | 5/2015 | Palti | |
| 9,655,669 B2 | 5/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 10,779,875 B2 | 9/2020 | Palti et al. | |
| 10,821,283 B2 | 11/2020 | Giladi et al. | |
| 10,953,209 B2 | 3/2021 | Story et al. | |
| 11,013,909 B2 | 5/2021 | Wenger et al. | |
| 11,020,585 B2 | 6/2021 | Alon et al. | |
| 11,097,101 B2 | 8/2021 | Wasserman et al. | |
| 11,103,698 B2 | 8/2021 | Chang et al. | |
| 11,109,773 B2 | 9/2021 | Urman et al. | |
| 11,154,707 B2 | 10/2021 | Bomzon et al. | |
| 11,160,977 B2 | 11/2021 | Naveh et al. | |
| 2005/0075701 A1 | 4/2005 | Shafer | |
| 2009/0247934 A1 | 10/2009 | Tracey et al. | |
| 2011/0152975 A1* | 6/2011 | Colthurst | A61N 1/32 607/76 |
| 2016/0038753 A1 | 2/2016 | Chomenky et al. | |
| 2018/0001075 A1 | 1/2018 | Kirson et al. | |
| 2018/0202991 A1 | 7/2018 | Giladi et al. | |
| 2019/0307781 A1 | 10/2019 | Krex et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0108031 A1 | 4/2020 | Borst et al. | |
| 2020/0114141 A1 | 4/2020 | Bomzon et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 | 5/2020 | Wasserman et al. | |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0269041 A1 | 8/2020 | Zeevi et al. | |
| 2020/0269042 A1 | 8/2020 | Gliadi et al. | |
| 2020/0269043 A1 | 8/2020 | Wasserman et al. | |
| 2020/0306531 A1 | 10/2020 | Tran et al. | |
| 2020/0330755 A1 | 10/2020 | Wasserman et al. | |
| 2020/0368525 A1 | 11/2020 | Maag et al. | |
| 2020/0391021 A1* | 12/2020 | Sachs | A61N 1/36132 |
| 2021/0000528 A1 | 1/2021 | Palti et al. | |
| 2021/0008367 A1 | 1/2021 | Giladi et al. | |
| 2021/0031031 A1 | 2/2021 | Wasserman et al. | |
| 2021/0038584 A1 | 2/2021 | Voloshin-Sela | |
| 2021/0060334 A1 | 3/2021 | Avraham et al. | |
| 2021/0069503 A1 | 3/2021 | Tran et al. | |
| 2021/0187277 A1 | 6/2021 | Wasserman et al. | |
| 2021/0196348 A1 | 7/2021 | Wasserman | |
| 2021/0199640 A1 | 7/2021 | Patel et al. | |
| 2021/0203250 A1 | 7/2021 | Wasserman | |
| 2021/0268247 A1 | 9/2021 | Story et al. | |
| 2021/0299440 A1 | 9/2021 | Deslauriers et al. | |
| 2021/0308446 A1 | 10/2021 | Alon et al. | |
| 2021/0330950 A1 | 10/2021 | Hagemann et al. | |
| 2021/0346694 A1 | 11/2021 | Wasserman et al. | |

OTHER PUBLICATIONS

Agnesi et al., "Deep Brain Stimulation: how does it work?," Handbook of Clinical Neurology, vol. 116, Chapter 4, pp. 39-54, 2013.

Bai et al., Tight control of respiration by NADH dehydrogenase NDS subunit gene expression in mouse mitochondria,: Molecular and Cellular Biology, vol. 20, No. 3, pp. 805-815, Feb. 2000.

Benson, "Tumor Treating Fields Technology: Alternating Electric Filed Therapy for the Treatment of Solid Tumors," Seminars in Oncology Nursing, vol. 34, No. 2, pp. 137-150 May 2018.

Bernard-Arnoux et al., "The cost-effectivess of tumor-treating fields therapy in patients with newly diagnosed glioblastoma," Neuro-Oncology, vol. 18, No. 8, pp. 1129-1136, May 2016.

Chaudhry et al., "NovoTTF-100A System (Tumor Treating Fields) transducer array layout planning for glioblastoma: a NovoTAL system user study." World Journal of Surgical Oncology, vol. 13, p. 316, 2015.

Chen et al., "Enrichr: interactive and collaborative HTML5 gene list enrichment analysis tool," BMC Bioinformatics, vol. 14, p. 128, 2013.

Chiken et al., "Mechanism of Deep Brain Stimulation: Inhibition, Excitation, or Disruption?," The Neuroscientist, vol. 22, No. 3, pp. 313-322, 2016.

Clark et al., "The effects of tumor treating fields and temozolomide in MGMT expressing and non-expressing patient-derived glioblastoma cells," Journal of Clinical Neuroscience, vol. 36, pp. 120-124, 2016.

Cucullo et al., "Very Low Intensity Alternating Current Decreases Cell Proliferation," Glia, vol. 51, pp. 65-72, 2005.

Gera et al., "Tumor Treating Fields Perturb the Localization of Septins and Cause Aberrant Mitotic Exit," PLOS One, vol. 10, p. e0125269, May 2015.

Giladi et al., "Mitotic Spindle Disruption by Alternating Electric Fields Leads to Improper Chromosome Segregation and Mitotic Catastrophe in Cancer Cells," Scientific Reports, vol. 5, p. 18046, Dec. 2015.

Giladi et al., "Tumor treating fields (TTFields) delay DNA damage repair following radiation treatment of glioma cells," Radiation Oncology, vol. 12, No. 206, pp. 1-13, 2017.

Hegi et al., "MGMT Gene Silencing and Benefit from Temozolomide in Glioblastoma," The New England Journal of Medicine, vol. 352, pp. 997-1003, Mar. 2005.

Hsu et al., "Identification of novel gene expression signature in lung adenocarcinoma by using next-generation sequencing data and bioinformatics analysis," Oncotarget, vol. 8, No. 62, p. 104831-104854, Sep. 2017.

Jang et al., "Cancer cell metabolism: implications for therapeutic targets," Experimental & Molecular Medicine, vol. 45, p. e45, Oct. 2013.

Jiang et al., "Butyrophilin-Like 9 (BTNL9) Suppresses Invasion and Correlates with Favorable Prognosis of Uveal Melanoma," Medical Science Monitor, vol. 25, pp. 3190-3198, 2019.

Jo et al., "Selective toxicity of tumor treating fields to melanoma: an in vitro and in vivo study," Cell Death Discovery, vol. 4, p. 46, 2018.

(56) References Cited

OTHER PUBLICATIONS

Julia et al., "An Efficient Platform for Astrocyte Differentiation from Human Induced Pluripotent Stem Cells," Stem Cell Reports, vol. 9, pp. 600-614, Aug. 2017.
Kessler et al., "Effects of tumor treating fields (TTFields) on glioblastoma cells are augmented by mitotic checkpoint inhibition," Cell Death Discovery, 5:12, 2019.
Kirson et al., "Alternating electric fields arrest cell proliferation in animal tumor models and human brain tumors", Proceedings of the National Academy of Sciences, Jun. 12, 2007, vol. 104(24), pp. 10152-7.
Kirson et al., "Chemotherapeutic treatment efficacy and sensitivity are increased by adjuvant alternating electric fields (TTFields)," BMC Medical Physics, vol. 9, No. 1, Jan. 2009.
Kirson et al.; "Disruption of cancer cell replication by alternating electric fields"; Cancer Research, 64(9): 3288-3295, May 2004.
Korshoej et al., "Importance of electrode position for the distribution of tumor treating fields (TTFields) in a human brain. Identification of effective layouts through systemic analysis of array positions for multiple tumor locations," PLOS One, vol. 13, p. e0201957, Aug. 2018.
Kuleshov et al., "Enricher: a comprehensive gene set enrichment analysis web server 2016 update," Nucleic Acids Research, vol. 44, pp. W90-W97, May 2016.
Lin et al., "Mitochondrial dysfunction and oxidative stress in neurodegenerative diseases," Nature, vol. 443, pp. 787-795, Oct. 2006.
Mukhtar et al., "Targeting Microtubules by Natural Agents for Cancer Therapy," Molecular Cancer Therapeutics, vol. 13, No. 2, pp. 275-284, Jan. 2014.
Neuhaus et al., "Alternating Electric Fields (TTFields) Activate Cav1.2 Channels in Human Glioblastoma Cells," Cancers, vol. 11, p. 110, 2019.
Porat et al., "Determining the Optimal Inhibitory Frequency for Cancerous Cells Using Tumor Treating Fields," Journal of Visualized Experiments, vol. 123, p. e55820, May 2017.
Rapp et al., "Recurrence Pattern Analysis of Primary Glioblastoma," World Neurosurgery, vol. 103, pp. 733-740, Jul. 2017.
Schwartzbaum et al., "Epidemiology and molecular pathology of glioma," Nature Reviews Neurology, vol. 2, No. 9, pp. 494-503, Sep. 2006.
Sebastiano et al., "Preclinical outcomes of Intratumoral Modulation Therapy for glioblastoma," Scientific Reports, vol. 8, p. 7301, 2018.
Shteingauz et al., "Induction of autophagy following TTFields application serves as a survival mechanism mediated by AMPK activation," Proceedings of the 109th Annual Meeting of the American Association for Cancer Research, Apr. 14-18, 2018, Chicago, Illinois, Abstract nr1343.
Silginer et al., "Biological activity of tumor-treating fields in preclinical glioma models," Cell Death and Disease, vol. 8, p. e2753, 2018.
Stupp et al., "Effect of Tumor-Treating Fields Plus Maintenance Temozolomide vs. Maintenance Temozolomide Alone on Survival in Patients with Glioblastoma: A Randomized Clinical Trial," JAMA, vol. 318, pp. 2306-2316, 2017.
Stupp et al., "NovoTTF-100A versus physician's choice chemotherapy in recurrent glioblastoma: A randomised phase III trial of a novel treatment modality," European Journal of Cancer, vol. 48, pp. 2192-2202, May 2012.
Stupp et al., "Radiotherapy plus Concomitant and Adjuvant Temozolomide for Glioblastoma," The New England Journal of Medicine, vol. 352, pp. 987-996, Mar. 2005.
Voloshin et al., "Alternating electric fields (TTFields) in combination with paclitaxel are therapeutically effective against ovarian cancer cells in vitro and in vivo," International Journal of Cancer, vol. 139, pp. 2850-2858, 2016.
Wenger et al., "A Review on Tumor-Treating Fields (TTFields): Clinical Implications Inferred From Computational Modeling," IEEE Reviews in Biomedical Engineering, vol. 11, pp. 195-207, 2018.
Wick, "TTFields: where does all the skepticism come from?," Neuro-Oncology, vol. 18, No. 3, pp. 303-305, 2016.
Xu et al., "In Vitro Validation of Intratumoral Modulation Therapy for Glioblastoma," Anticancer Research, vol. 36, pp. 71-80, 2016.
Yamazaki et al., "A Butyrophilin Family Member Critically Inhibits T Cell Activation," The Journal of Immunology, vol. 185, pp. 5907-5914, 2010.
Yang et al., "Membrane potential and cancer progression," Frontiers in Physiology, vol. 4, Article 185, Jul. 2013.

* cited by examiner

| Gene Symbol | Gene Symbol |
|---|---|
| CAPNS1 | UBE2D2 |
| HIST2H2AC | SELT |
| CTSB | RNF13 |
| TRAM1 | TXNRD1 |
| ND5 | HIST2H2AA3 |
| TMEM138 | GNB1 |
| NUTF2 | ALYREF |
| SRM | HDLBP |
| EIF4H | HIST2H4A |
| BTNL9 | TMEM123 |
| EIF4G2 | CDK4 |
| CANX | SH3BGRL3 |
| RAB7A | MAT2A |
| DDX5 | MAX |
| CALR | HIST1H2BJ |
| PPP4R1 | GDI2 |
| SDCBP | SLC25A6 |
| HNRNPH1 | SLC25A6 |
| PA2G4 | YIF1B |
| PDP1 | HIST1H2AE |
| SEP15 | HIST1H2BK |
| PTP4A1 | EEF1D |
| HIST2H2BF | PSMC2 |
| HIST2H2AA4 | ANAPC15 |
| HIST2H4B | ITGB1 |

Figure 7

TREATING AUTOINFLAMMATORY AND MITOCHONDRIAL DISEASES USING AN ALTERNATING ELECTRIC FIELD

CROSS REFERENCE TO RELATED APPLICATIONS

This application is a continuation-in-part of U.S. patent application Ser. No. 17/333,509 (filed on May 28, 2021), which is a continuation of U.S. patent application Ser. No. 16/560,134 (filed on Sep. 4, 2019), now U.S. Pat. No. 11,020,585, which claims the benefit of U.S. Provisional Application 62/728,174 (filed on Sep. 7, 2018). This Application also claims the benefit of U.S. Provisional Application 63/045,378 filed Jun. 29, 2020, U.S. Provisional Application 63/045,390 filed Jun. 29, 2020, and U.S. Provisional Application 63/045,980 filed Jun. 30, 2020, all which are incorporated herein by reference in their entirety. Patents, publications, and appendices cited herein are hereby incorporated by reference in their entirety.

BACKGROUND

In autoimmune diseases, a person's own immune system mistakenly attacks specific portions of the person's body. Examples of T cells dependent autoimmune diseases include: diabetes mellitus type I (where the immune system attacks beta cells in the pancreas); rheumatoid arthritis (where the immune system attacks the synovial membranes of joints); multiple sclerosis (where the immune system attacks the central nervous system); polymyositis (where the immune system attacks certain muscles); lupus nephritis (where the immune system attacks the glomeruli in the kidney); and Rasmussen's encephalitis (where the immune system attacks portions of the brain). Autoimmune diseases relate to the adaptive immune system which can respond to specific pathogens.

In contrast, autoinflammatory diseases are disorders of the innate immune system. The innate immune system is non-specific to particular pathogens and provides a first line of defense that responds to general features of pathogens and can activate general protective systems such as the complement system. Examples of autoinflammatory diseases include, but are not limited to, Crohn's disease, intestinal inflammation, irritable bowel syndrome (IBS), and ulcerative colitis (UC). Autoinflammatory diseases can be caused by genetic mutations (e.g., Familial Mediterranean Fever (MEFV), cryopyrin associated periodic syndrome (NLRP3), and the TNF-receptor associated periodic syndrome (TNFRSF1A)).

Mitochondrial diseases are metabolic disorders typically related to mutations in genes related to mitochondrial functions resulting in aberrant energy production in the cell. These diseases can have wide-ranging effects on the brain, heart, liver, and/or central nervous system. Mitochondrial complex I deficiency, for example, can result in abnormal reduction and oxidative phosphorylation in cells. Mitochondrial complex I deficiency can effect many organs and systems of the body, particularly the nervous system, the heart, and muscular system.

In a separate field, it has been established that tumors (e.g., glioblastoma) can be treated by applying a 200 kHz alternating electric field to the tumor. This is described in U.S. Pat. Nos. 7,016,725 and 7,565,205, each of which is incorporated herein by reference in its entirety. And in the context of treating tumors, these alternating electric fields are referred to as "tumor treating fields" or "TTFields." TTFields are delivered using a wearable and portable device called Optune® made by Novocure™.

SUMMARY OF THE INVENTION

One aspect of the invention is directed to a first method of preventing or minimizing damage from an autoimmune disease in a target region of a subject's body. The first method comprises positioning a plurality of electrodes in or on the subject's body positioned with respect to the target region so that application of an AC voltage between the plurality of electrodes will impose an alternating electric field through tissue that is being attacked by the autoimmune disease in the target region; and applying an AC voltage between the plurality of electrodes for an interval of time, such that an alternating electric field is imposed through the tissue for the interval of time. The alternating electric field has a frequency and a field strength such that when the alternating electric field is imposed in the tissue for the interval of time, the alternating electric field inhibits proliferation of T cells in the tissue to an extent that reduces damage that is caused by the autoimmune disease.

In some instances of the first method, the plurality of electrodes is also positioned with respect to the subject's body so that the alternating electric field is imposed in at least one draining lymph node associated with the tissue that is being attacked.

In some instances of the first method, the autoimmune disease is type 1 diabetes, and the plurality of electrodes is positioned with respect to the subject's body so that the alternating electric field is imposed in a liver or a pancreas. In some of these instances, the plurality of electrodes is also positioned with respect to the subject's body so that the alternating electric field is imposed in at least one pancreatic draining lymph node.

In some instances of the first method, the autoimmune disease is multiple sclerosis, and the plurality of electrodes is positioned with respect to the subject's body so that the alternating electric field is imposed in at least one lesion in the subject's central nervous system.

In some instances of the first method, the autoimmune disease is polymyositis, and the plurality of electrodes is positioned with respect to the subject's body so that the alternating electric field is imposed in at least one muscle of the subject. In some of these instances, the plurality of electrodes is also positioned with respect to the subject's body so that the alternating electric field is imposed in at least one draining lymph node associated with the at least one muscle.

In some instances of the first method, the autoimmune disease is rheumatoid arthritis, and the plurality of electrodes is positioned with respect to the subject's body so that the alternating electric field is imposed in at least one joint of the subject. In some of these instances, the plurality of electrodes is also positioned with respect to the subject's body so that the alternating electric field is imposed in at least one draining lymph node associated with the at least one joint.

In some instances of the first method, the autoimmune disease is Rasmussen encephalitis, and the plurality of electrodes is positioned with respect to the subject's body so that the alternating electric field is imposed in an affected hemisphere of the subject's brain.

In some instances of the first method, the autoimmune disease is lupus nephritis, and the plurality of electrodes is positioned with respect to the subject's body so that the alternating electric field is imposed in at least one kidney of the subject. In some of these instances, the plurality of electrodes is also positioned with respect to the subject's body so that the alternating electric field is imposed in at least one draining lymph node associated with the at least one kidney.

In some instances of the first method, the positioning comprises positioning a first set of electrodes in or on the subject's body and positioning a second set of electrodes in or on the subject's body. The first set of electrodes is positioned with respect to the target region so that application of an AC voltage between the electrodes of the first set will impose an alternating electric field with a first orientation through the tissue that is being attacked by the autoimmune disease in the target region. The second set of electrodes is positioned with respect to the target region so that application of an AC voltage between the electrodes of the second set will impose an alternating electric field with a second orientation through the tissue. The first orientation and the second orientation are different. The applying comprises repeating, in an alternating sequence, (a) applying a first AC voltage between the electrodes of the first set, such that an alternating electric field with the first orientation is imposed through the tissue and (b) applying a second AC voltage between the electrodes of the second set, such that an alternating electric field with the second orientation is imposed through the tissue. The alternating electric field with the first orientation has a frequency and a field strength such that when the alternating electric field with the first orientation is imposed in the tissue, the alternating electric field with the first orientation inhibits proliferation of T cells in the tissue. The alternating electric field with the second orientation has a frequency and a field strength such that when the alternating electric field with the second orientation is imposed in the tissue, the alternating electric field with the second orientation inhibits proliferation of T cells in the tissue. The inhibited proliferation of T cells in the tissue reduces damage that is caused by the autoimmune disease.

Optionally, in the instances of the first method described in the previous paragraph, the first and second sets of electrodes may also be positioned with respect to the subject's body so that the alternating electric fields with the first and second orientations are also imposed in at least one draining lymph node associated with the tissue that is being attacked. Optionally, in the instances of the first method described in the previous paragraph, the first orientation is offset from the second orientation by at least 60°.

Another aspect of the invention is directed to a second method of preventing or minimizing damage from an autoimmune disease in tissue that is being attacked by the autoimmune disease. The second method comprises positioning a plurality of electrodes in or on a subject's body positioned with respect to at least one draining lymph node associated with the tissue that is being attacked so that application of an AC voltage between the plurality of electrodes will impose an alternating electric field through the at least one draining lymph node; and applying an AC voltage between the plurality of electrodes for an interval of time, such that an alternating electric field is imposed through the at least one draining lymph node for the interval of time. The alternating electric field has a frequency and a field strength such that when the alternating electric field is imposed in the at least one draining lymph node for the interval of time, the alternating electric field inhibits proliferation of T cells in the at least one draining lymph node to an extent that reduces damage that is caused by the autoimmune disease.

In some instances of the second method, the positioning comprises positioning a first set of electrodes in or on the subject's body and positioning a second set of electrodes in or on the subject's body. The first set of electrodes is positioned with respect to the at least one draining lymph node associated with the tissue that is being attacked so that application of an AC voltage between the electrodes of the first set will impose an alternating electric field with a first orientation through the at least one draining lymph node, and the second set of electrodes is positioned with respect to the at least one draining lymph node so that application of an AC voltage between the electrodes of the second set will impose an alternating electric field with a second orientation through the at least one draining lymph node. The first orientation and the second orientation are different. The applying comprises repeating, in an alternating sequence, (a) applying a first AC voltage between the electrodes of the first set, such that an alternating electric field with the first orientation is imposed through the at least one draining lymph node and (b) applying a second AC voltage between the electrodes of the second set, such that an alternating electric field with the second orientation is imposed through the at least one draining lymph node. The alternating electric field with the first orientation has a frequency and a field strength such that when the alternating electric field with the first orientation is imposed in the at least one draining lymph node, the alternating electric field with the first orientation inhibits proliferation of T cells in the at least one draining lymph node. The alternating electric field with the second orientation has a frequency and a field strength such that when the alternating electric field with the second orientation is imposed in the at least one draining lymph node, the alternating electric field with the second orientation inhibits proliferation of T cells in the at least one draining lymph node. The inhibited proliferation of T cells in the at least one draining lymph node reduces damage that is caused by the autoimmune disease.

Optionally, in the instances of the second method described in the previous paragraph, the first orientation is offset from the second orientation by at least 60°.

Optionally, in any of the instances of the first or second methods described above, each of the plurality of electrodes is capacitively coupled to the subject's body. Optionally, in any of the instances of the first or second methods described above, the positioning and the applying are implemented after it has been determined that an acute phase of the autoimmune disease is starting.

Optionally, any of the instances of the first or second methods described above further comprise treating the autoimmune disease with a therapeutically effective drug regimen.

Optionally, in any of the instances of the first or second methods described above, the alternating electric field has a frequency of about 200 kHz. Optionally, in any of the instances of the first or second methods described above, the alternating electric field has a frequency between 50 and 500 kHz. Optionally, in any of the instances of the first or second methods described above, the alternating electric field has a field strength between 1 and 5 V/cm RMS. Optionally, in any of the instances of the first or second methods described above, the tissue is tumor-free.

Another aspect of the invention is directed to a third method of treating an autoinflammatory disease in a target region of a subject's body. The third method comprises positioning a plurality of electrodes in or on the subject's body, positioned with respect to the target region so that application of an AC voltage between the plurality of electrodes will impose an alternating electric field through tissue that is being affected by the autoinflammatory disease in the target region; and applying an AC voltage between the plurality of electrodes for an interval of time, such that an alternating electric field is imposed through the tissue for the interval of time. In this aspect, the alternating electric field has a frequency and a field strength such that when the alternating electric field is imposed in the tissue for the interval of time, the alternating electric field treats inflammation in the tissue.

In some instances of the third method, the autoinflammatory disease is Crohn's disease, and the plurality of electrodes is positioned with respect to the subject's body so that the alternating electric field is imposed in the subject's gastrointestinal system.

In some instances of the third method, the autoinflammatory disease is intestinal inflammation, and the plurality of electrodes is positioned with respect to the subject's body so that the alternating electric field is imposed in the subject's gastrointestinal system.

In some instances of the third method, the autoimmune disease is irritable bowel syndrome, and the plurality of electrodes is positioned with respect to the subject's body so that the alternating electric field is imposed in the subject's gastrointestinal system.

In some instances of the third method, the autoinflammatory disease is ulcerative colitis, and the plurality of electrodes is positioned with respect to the subject's body so that the alternating electric field is imposed in the subject's gastrointestinal system.

In some instances of the third method, the autoimmune disease is Familial Mediterranean Fever, and the plurality of electrodes is positioned with respect to the subject's body so that the alternating electric field is imposed in the subject's abdomen.

In some instances of the third method, the positioning comprises positioning a first set of electrodes in or on the subject's body, wherein the first set of electrodes is positioned with respect to the target region so that application of an AC voltage between the electrodes of the first set will impose an alternating electric field with a first orientation through tissue that is being affected by the autoinflammatory disease in the target region. The positioning also comprises positioning a second set of electrodes in or on the subject's body, wherein the second set of electrodes is positioned with respect to the target region so that application of an AC voltage between the electrodes of the second set will impose an alternating electric field with a second orientation through the tissue, wherein the first orientation and the second orientation are different.

In these instances, the applying comprises repeating, in an alternating sequence, (a) applying a first AC voltage between the electrodes of the first set, such that an alternating electric field with the first orientation is imposed through the tissue and (b) applying a second AC voltage between the electrodes of the second set, such that an alternating electric field with the second orientation is imposed through the tissue. The alternating electric field with the first orientation has a frequency and a field strength such that when the alternating electric field with the first orientation is imposed in the tissue, the alternating electric field with the first orientation inhibits inflammation in the tissue. The alternating electric field with the second orientation has a frequency and a field strength such that when the alternating electric field with the second orientation is imposed in the tissue, the alternating electric field with the second orientation inhibits inflammation in the tissue.

In some instances of the third method, the first orientation is offset from the second orientation by at least 60°.

Some instances of the third method further comprise treating the autoinflammatory disease with a therapeutically effective drug regimen.

In some instances of the third method, the alternating electric field has a frequency between 50 and 500 kHz. In some instances of the third method, the tissue is tumor-free.

In some instances of the third method, the tissue is located in an organ selected from the group consisting of heart, pancreas, liver, lung, kidney, brain, and intestine.

In some instances of the third method, a level of butyrophilin protein in the tissue is increased by at least 2-fold compared to cells of a tissue that is not exposed to the alternating electric fields. Optionally, in these instances, the butyrophilin protein is encoded by BTNL9.

In some instances of the third method, the interval of time is at least 72 hours.

Another aspect of the invention is directed to a fourth method of treating damage from a mitochondrial disease in a target region of a subject's body. The fourth method comprises positioning a plurality of electrodes in or on the subject's body, positioned with respect to the target region so that application of an AC voltage between the plurality of electrodes will impose an alternating electric field through tissue that is being affected by the mitochondrial disease in the target region. The AC voltage is applied between the plurality of electrodes for an interval of time, such that an alternating electric field is imposed through the tissue for the interval of time. The alternating electric field has a frequency and a field strength such that when the alternating electric field is imposed in the tissue for the interval of time, the alternating electric field treats the mitochondrial disease in the tissue.

In some instances of the fourth method, the mitochondrial disease is Nonalcoholic fatty liver disease (NAFLD), and the plurality of electrodes is positioned with respect to the subject's body so that the alternating electric field is imposed in the subject's liver.

In some instances of the fourth method, a level of MT-ND5 protein in cells of the tissue is reduced by at least 2-fold compared to cells of a tissue that is not exposed to the alternating electric fields.

In some instances of the fourth method, the positioning comprises positioning a first set of electrodes in or on the subject's body, wherein the first set of electrodes is positioned with respect to a target region so that application of an AC voltage between the electrodes of the first set will impose an alternating electric field with a first orientation through a tissue that is being affected by the mitochondrial disease in the target region. The positioning also comprises positioning a second set of electrodes in or on the subject's body, wherein the second set of electrodes is positioned with respect to the target region so that application of an AC voltage between the electrodes of the second set will impose an alternating electric field with a second orientation through the tissue, wherein the first orientation and the second orientation are different. The applying comprises repeating, in an alternating sequence, (a) applying a first AC voltage between the electrodes of the first set, such that an alternating electric field with the first orientation is imposed through the tissue and (b) applying a second AC voltage between the electrodes of the second set, such that an alternating electric field with the second orientation is imposed through the tissue. The alternating electric field with the first orientation has a frequency and a field strength such that when the alternating electric field with the first orientation is imposed in the tissue, the alternating electric field with the first orientation treats the mitochondrial disease in the tissue. The alternating electric field with the second orientation has a frequency and a field strength such that when the alternating electric field with the second orientation is imposed in the tissue, the alternating electric field with the second orientation treats the mitochondrial disease in the tissue.

In some instances of the fourth method, the first orientation is offset from the second orientation by at least 60°.

Some instances of the fourth method further comprise treating the mitochondrial disease with a therapeutically effective drug regimen.

In some instances of the fourth method, the alternating electric field has a frequency between 50 and 500 kHz. In some instances of the fourth method, the tissue is tumor-free.

BRIEF DESCRIPTION OF THE DRAWINGS

FIG. 7 provides a table of top 50 differentially expressed genes from TTFields-treated cells versus sham controls in GIN-31 and KNS42 cell lines;

Various embodiments are described in detail below with reference to the accompanying drawings, wherein like reference numerals represent like elements.

DESCRIPTION OF THE PREFERRED EMBODIMENTS

Part 1-Treatment of Autoimmune Diseases

Figure 1:
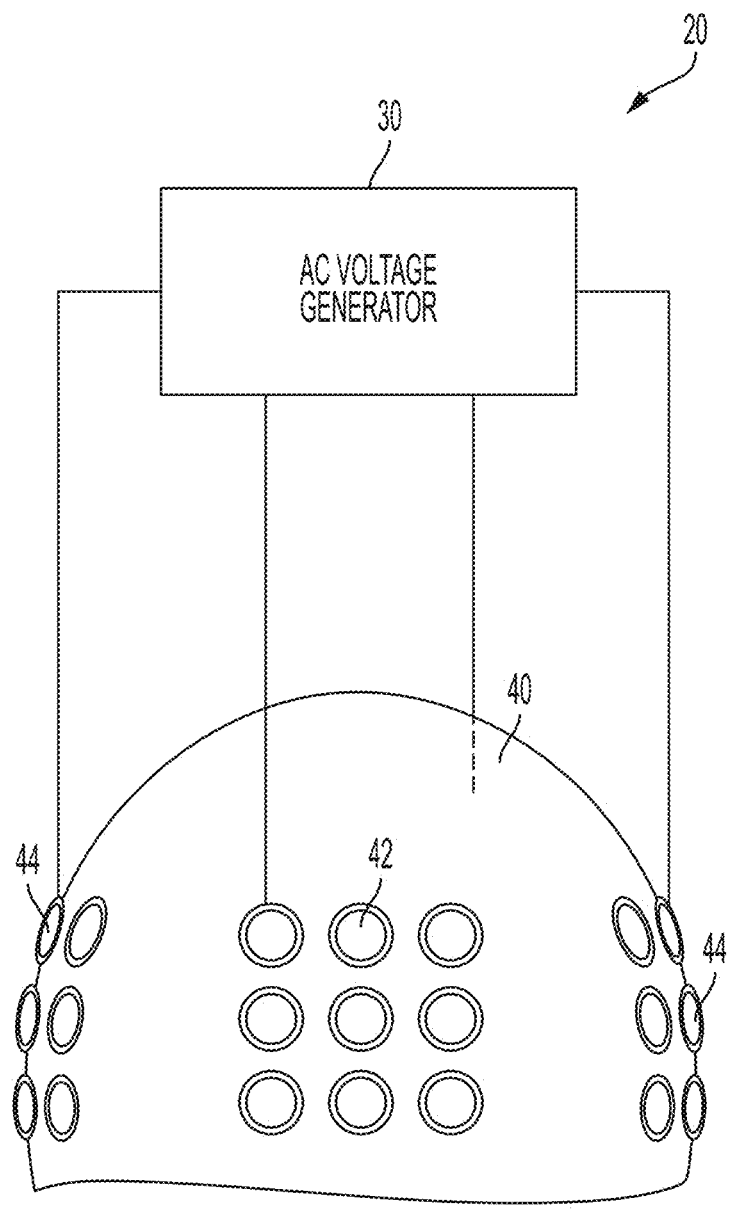
FIG. 1 is a schematic representation of a system for applying alternating electric fields to tissue in a person's brain that is used to minimize damage to brain tissue caused by an autoimmune disease.

In some embodiments described below, a system that is similar to the Optune® system for treating tumors with TTFields is used to treat an autoimmune disease instead of treating a tumor. Although use of the Optune® system for treating glioblastoma is well-understood by persons skilled in the relevant arts, it will be described here briefly for completeness. Four arrays of capacitively coupled electrodes (also called "transducer arrays") are positioned on the subject' shaved head (e.g., one on the front, one on the back, one on the right side, and one on the left side). An AC voltage generator applies an AC voltage at 200 kHz between the front/back pair of electrode arrays for one second, then applies an AC voltage at the same frequency between the right/left pair of electrode arrays for one second, and repeats this two-step sequence for the duration of the treatment. This induces TTFields in the first and second orientations through the subject's brain in an alternating sequence. The electrode arrays are positioned so that the first orientation and the second direction are offset by a significant amount (e.g., at least 60°, or at least 80°).

T cells in the body's immune system can play a very important role in combatting tumors. In view of this, studies were done to ascertain whether TTFields might interfere with the operation of T cells. One such study concluded that "As the presence of polyfunctional T cells is associated with effective anti-tumoral responses, a single-cell level polyfunctionality analysis of activated T cells was performed. The analysis demonstrated that under TTFields conditions non proliferating cells retained all other combinations of immune functions. TTFields were found to have a minor effect on the viability of un-activated T cells. In activated cells, there was a moderate effect on cells that did not attempt to proliferate, but TTFields substantially reduced the viability rate of cells that had proliferated. These findings were true for both helper and cytotoxic T cells." Evaluating the In-Vitro Effects of Tumor Treating Fields on T Cell Responses, G. Diamant et al., Proceedings of the AACR, Volume 58, Abstract #617, April 2017.

In the context of treating tumors, because fewer T cells will be available to attack the tumor cells, reducing the proliferation of T cells is a drawback. But in the context of treating an autoimmune disease, this very same drawback is advantageously transformed into a benefit. More specifically, this application explains how autoimmune diseases can be treated by using an alternating electric field ("AEF")

to inhibit the proliferation of T cells, which are key participants in the immune system's attack on a person's body. Because AEFs can inhibit the proliferation of T cells, AEFs can prevent or reduce the damage that T cells inflict on a person's body in the context of an autoimmune disease, which can slow the progression of the disease.

Furthermore, many autoimmune diseases have distinct stages during which the immune system attacks tissue in a subject's body. For these autoimmune diseases, the application of the AEFs may be timed to coincide with the intervals of time during which the immune system is actively attacking the relevant tissue. In many preferred embodiments, the electrodes are positioned to maximize the electric field in the tissue that is being attacked by the immune system. The concepts described in this section are applicable to a wide variety of autoimmune diseases, including but not limited to the diseases identified individually below.

In type 1 diabetes, the immune system damages the beta cells of the pancreas in stage 1 (where the subjects are still normal glycemic) and stage 2 (dysglycemia from loss of functional beta cell mass), so the AEFs should be applied to the relevant anatomy during those stages of the disease to slow the disease's progression. But once type 1 diabetes has progressed to stage 3, the subject's beta cells have already been damaged beyond repair, so there is no point in continuing treatment. Because the immune system is attacking the pancreas, the best positioning for the electrodes is to place one pair of electrodes on the subject's body in front of and behind the pancreas and/or the pancreatic draining lymph nodes, and the second pair of electrodes on the sides of the subject's body at a height that corresponds to the pancreas and/or the pancreatic draining lymph nodes.

In multiple sclerosis (MS), the immune system attacks myelinated axons in the central nervous system. With this disease, the AEFs should be applied to the relevant anatomy of subjects who have been diagnosed with secondary progressive MS, primary progressive MS, relapsing-remitting MS, or progressive relapsing MS to slow the disease's progression. As for positioning of the electrodes, because it may be impractical to apply AEFs to the entire central nervous system, lesions in the CNS may be detected using MRI, and the AEFs may be imposed only in those regions where the lesions were detected. Alternatively, the AEFs could be applied continuously to the subject's scalp as a prophylactic measure to prevent formation of brain lesions.

In polymyositis (PM), the immune system attacks a person's muscles, especially the muscles of the hips, thighs, upper arms, shoulder, neck, and the top part of the back. With this disease, the AEFs should be applied to the regions noted above and/or to associated draining lymph nodes to slow the disease's progression. For this disease, the electrodes may be positioned along strip-shaped regions that run in a proximal-to-distal direction along the body parts noted above, e.g., with one pair of electrodes positioned in front of and in back of the relevant body part, and a second pair of electrodes positioned on the right and left sides of the relevant body part.

In rheumatoid arthritis (RA), the immune system attacks a person's joints (e.g. knees, hips, shoulders, elbows, wrists, ankles, etc.). With this disease, the AEFs should be applied in subjects who have been diagnosed with polycyclic or progressive RA to the regions noted above and/or to associated draining lymph nodes to slow the disease's progression. The electrodes should be positioned in the vicinity of the joints during active disease and as a prophylactic measure during remission period in polycyclic RA. Note that the electrode positioning configurations disclosed in US 2018/0001075, which is incorporated herein by reference in its entirety, may be used to apply the AEFs to certain joints (e.g. knees, elbows, and wrists).

In Rasmussen encephalitis (RE), the immune system attacks a single hemisphere of a person's brain. This disease typically progresses through three stages: the prodromal stage, the acute stage, and the residual stage. With this disease, the AEFs should be applied to the affected hemisphere of the brain of subjects who had been diagnosed with the acute stage of RE to slow the progression of the disease. Once the disease has progressed to the residual stage, treatment may be discontinued. The electrodes should be positioned on the subject's scalp in order to maximize the field in the affected hemisphere. Many of the approaches for determining the optimal placement of the electrodes in the context of glioblastoma may be used in the context of RE.

In lupus nephritis the immune system attacks a person's kidneys. The best positioning for the electrodes for this disease is to place one pair of electrodes on the subject's body in front of and behind the kidneys and/or associated draining lymph nodes, and the second pair of electrodes on the sides of the subject's body at a height that corresponds to the kidneys and/or the associated draining lymph nodes.

For any of the diseases described above, it is preferable to treat the afflicted portions of the subject's body with AEFs for significant durations of time (e.g., at least 75% of the time, which comes to at least 18 hours a day).

Many autoimmune diseases, including some of the diseases identified above, affect portions of the body (e.g., pancreas, kidneys, etc.) that have associated draining lymph nodes. As most T cell proliferation takes place in the draining lymph nodes, treatment of these autoimmune disease using AEFs may be accomplished by either (a) applying the AEF's to the relevant body part alone (e.g., pancreas, kidneys, etc.) (b) applying the AEF's to the associated draining lymph node or nodes alone; or (c) applying the AEFs to both the relevant body part and the associated draining lymph node or nodes. The decision as to which lymph node or nodes are associated with the relevant body part may be based upon the literature (i.e., in situations where the association between a body part and a specific lymph node is known in medical literature) or personalized to each individual subject using imaging (e.g., CT, MRI, ultrasound, etc.).

FIG. 1 depicts an example system 20 for applying AEFs to tissue in a person's brain that is used to minimize damage to brain tissue caused by an autoimmune disease (e.g., Rasmussen encephalitis). The system 20 includes an AC voltage generator 30, a first set of electrodes 44 positioned on the right and left side of the head, and a second set of electrodes 42 positioned on the front and back of the head. (Because FIG. 1 depicts the front view of the scalp 40, the electrodes 42 that are positioned on the back of the head are not visible in this view.) In the illustrated embodiment, each of the electrodes 42, 44 includes nine circular elements that are wired in parallel. But in alternative embodiments, a different number of elements and/or elements with different shapes may be used, depending on the anatomical location where the electrodes will be positioned for any given autoimmune disease.

To use this system, the first set of electrodes 44 is applied to the subject's body (i.e., on the right and left sides of the head in the illustrated embodiment). The first set of electrodes 44 is positioned with respect to the target region so that application of an AC voltage between the electrodes 44 will impose an alternating electric field with a first orientation (i.e., right to left in the illustrated embodiment) through tissue that is being attacked by the autoimmune disease in the target region (i.e., the brain in the illustrated embodiment). The second set of electrodes 42 is also applied to the subject's body (i.e., on the front and back of the head in the illustrated embodiment). The second set of electrodes is positioned with respect to the target region so that application of an AC voltage between the electrodes 42 will impose an alternating electric field with a second orientation through the tissue (i.e., front to back in the illustrated embodiment). The first orientation and the second orientation are different (and are roughly perpendicular in the illustrated embodiment).

After the first and second set of electrodes 42, 44 have been applied to the subject's body, the AC voltage generator 30 repeats the following steps in an alternating sequence: (a) applying a first AC voltage between the electrodes of the first set 44, such that an alternating electric field with the first orientation is imposed through the tissue and (b) applying a second AC voltage between the electrodes of the second set 42, such that an alternating electric field with the second orientation is imposed through the tissue. The alternating electric field with the first orientation has a frequency and a field strength such that when the alternating electric field with the first orientation is imposed in the tissue, the alternating electric field with the first orientation inhibits proliferation of T cells in the tissue. And the alternating electric field with the second orientation has a frequency and a field strength such that when the alternating electric field with the second orientation is imposed in the tissue, the alternating electric field with the second orientation inhibits proliferation of T cells in the tissue. The inhibition of the proliferation of T cells in the tissue reduces damage that is caused by the autoimmune disease.

In some embodiments, all the electrodes are positioned on the subject's body (as depicted in FIG. 1); in other embodiments, all the electrodes may be implanted in the subject's body (e.g., just beneath the subject's skin, or in the vicinity of the organ being treated); and in other embodiments, some of the electrodes are positioned on the subject's skin and the rest of the electrodes are implanted in the subject's body.

The same frequency that is used in the Optune® system to treat glioblastoma (i.e., 200 kHz) may also be used to treat an autoimmune disease by inhibiting the proliferation of T cells, as described above. But in alternative embodiments, a different frequency may be used. For example, the frequency of the AEFs that are used to treat autoimmune diseases may be between 100 and 300 kHz, between 50 and 500 kHz, or between 25 kHz and 1 MHz. The optimal frequency may be determined experimentally for each individual autoimmune disease. Preferably, care is taken to ensure that the AEFs at the selected frequency do not adversely heat portions of the subject's body.

The field strength of the AEFs may be between 0.2 and 1 V/cm RMS, between 1 and 5 V/cm RMS, or between 5 and 25 V/cm RMS. The optimal field strength may be determined experimentally for each individual autoimmune disease. Here again, care is preferably taken to ensure that the AEFs at the field strength that is being used do not adversely heat portions of the subject's body.

The orientation of the AEFs may be switched at one second intervals between two different orientations by applying AC voltages between two different sets of electrodes, as done in the Optune® system. But in alternative embodiments, the orientation of the AEFs can be switched at a faster rate (e.g., at intervals between 1 and 1000 ms) or at a slower rate (e.g., at intervals between 1 and 100 seconds). In other alternative embodiments, the electrodes need not be arranged in pairs. See, for example, the electrode positioning described in U.S. Pat. No. 7,565,205, which is incorporated herein by reference. In other alternative embodiments, the orientation of the field need not be switched at all, in which case only a single pair of electrodes is required.

In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body.

Optionally, thermal sensors (not shown) may be included at the electrodes, and the AC voltage generator 30 can be configured to decrease the amplitude of the AC voltages that are applied to the electrodes if the sensed temperature at the electrodes gets too high.

In some embodiments, one or more additional pairs of electrodes may be added and included in the sequence. In other embodiments, the field is only imposed in the target region with a single orientation, in which case the alternating sequence described above may be replaced with a continuous AC signal that is applied to a single set of electrodes (e.g., positioned on opposite sides of the target region).

Note that while FIG. 1 depicts an embodiment in which the AEFs are applied to the brain, the AEFs may be applied to different portions of a subject's body as described above in alternative embodiments.

The AEFs may be used to treat an autoimmune disease in tissue (e.g., the brain of a first person with RE) that is tumor free. Alternatively, the AEFs may be used to treat an autoimmune disease in tissue that contains a tumor (e.g., the brain of a different person with both RE and a glioblastoma).

Finally, AEF-based autoimmune therapy may optionally be combined with conventional drugs that are used to treat the respective disease.

Part 2-Treatment of Autoinflammatory Disease

Autoinflammatory diseases arise from the pathophysiology of the innate immune system and include disorders resulting in overproduction of proinflammatory cytokines and downstream, multisite inflammatory responses leading to hereditary periodic fevers, granulomatous disorders, and pyogenic diseases. See, e.g., Rigante et al. Untangling the web of systemic autoinflammatory diseases. *Mediators Inflamm.* 2014;2014:948154. doi:10.1155/2014/948154. Autoinflammatory diseases include conditions such as Crohn's disease, irritable bowel syndrome (IBS), and ulcerative colitis. Other autoinflammatory diseases include Familial Mediterranean fever (FMF), cryopyrin-associated periodic syndromes (CAPS), tumor necrosis factor (TNF)-receptor associated periodic syndrome (TRAPS), mevalonate kinase deficiency (MKD), pyogenic arthritis pustulosis acne (PAPA) syndrome, deficiency of interleukin-1 receptor antagonist (DIRA), NLRP12-related periodic fever and periodic fever aphthosis pharyngitis adenitis (PFAPA) syndrome.

Autoinflammatory diseases result from an overactive systemic inflammatory response as part of a first line, general response to infection or injury. In contrast, autoimmune diseases arise from the pathophysiology of the adaptive immune system resulting in production of B cells and T cells that lose the ability to differentiate self from non-self. In certain cases, autoinflammatory diseases are caused by genetic mutations while in other cases, immunodeficiency may play a role. Pathak S et al., *Autoinflammatory diseases:* update on classification diagnosis and management, Journal of Clinical Pathology 2017;70:1-8; ter Haar N et al., *Treatment of autoinflammatory diseases: results from the Eurofever Registry and a literature review*, Annals of the Rheumatic Diseases 2013;72:678-685.

Crohn's disease is an autoinflammatory disease resulting from inflammation of the bowel leading to abdominal pain, severe diarrhea, fatigue, weight loss and malnutrition.

Intestinal inflammation encompasses autoinflammatory diseases resulting from inflammation of the digestive tract leading to abdominal pain, severe diarrhea, fatigue, weight loss and malnutrition.

Irritable bowel syndrome is an autoinflammatory disease resulting from inflammation of the colon or rectum leading to abdominal pain, severe diarrhea, fatigue, weight loss and malnutrition.

Ulcerative colitis is a form of irritable bowel syndrome resulting in sores on the lining of the colon and rectum.

Familial Mediterranean Fever is a genetic disorder caused by a mutation in the MFEV gene. The MFEV gene has homology with butyrophilin. FMF French Consortium, A candidate gene for familial Mediterranean fever, Nat Genet, 1997 Sep;17(1):25-31. doi: 10.1038/ng0997-25. The disease results in painful inflammation in the abdomen, chest, or joints.

Figure 11A:
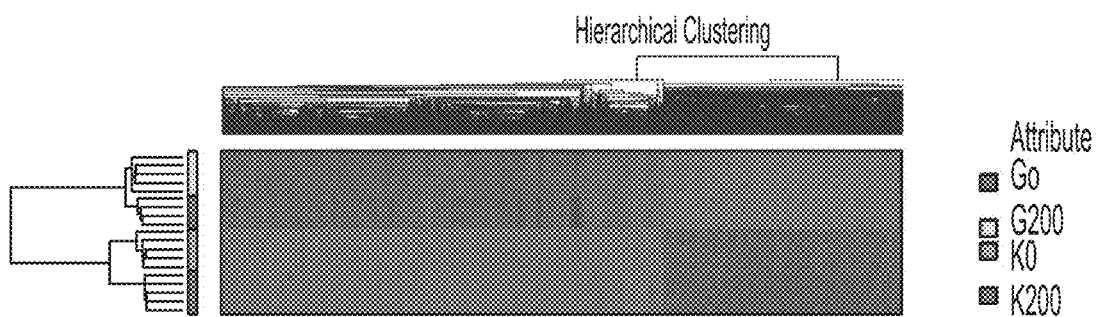
FIG. 11A shows the exemplary results of an experiment where KNS42 and GIN-31 cell lines were treated for 72 hours at the determined optimal frequency with TTFields and gene expression changes were assessed using Clariom™ S Assay arrays.
Figure 11B:
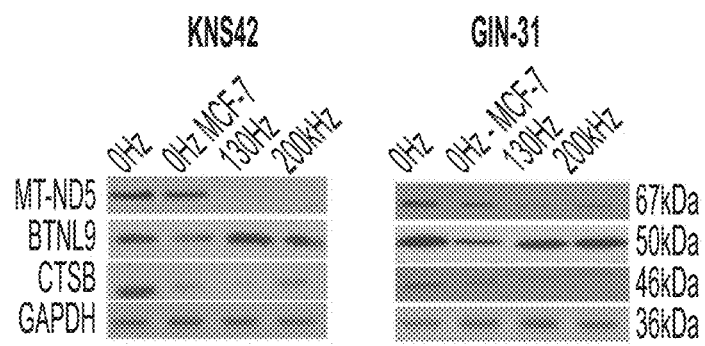
FIG. 11B is an exemplary Western blot showing corresponding protein level expression in KNS42 and GIN-31 cell lines.

As described herein, BTNL9 is the most upregulated gene in response to exposure to TTFields in an analysis of GBM cell lines (FIG. 11A). Upregulation of BTNL9 mRNA is correlated with upregulation of BTNL9 protein expression as shown in FIG. 11B where BTNL9 protein is increased by at least 2 fold following exposure to TTFields for 72 hours at 130 kHz and 200 kHz.

As discussed herein, and shown in FIG. 11A, application of TTFields to glioblastoma cell lines significantly increased expression of the Butyrophilin-like 9 (BTNL9). BTNL9 is a known inhibitor of the immune system. Yamazaki et al. A Butyrophilin Family member critically inhibits T cell proliferation. The Journal of Immunology, 2010, 185. BTNL9 expression is associated with inflammation and colon cancer and decreased expression of BTNL9 is associated with the autoinflammatory disease ulcerative colitis (UC). Lebrero-Fernández, C., et al., *Altered expression of Butyrophilin (BTN) and BTN-like (BTNL) genes in intestinal inflammation and colon cancer*, Immunity, Inflammation and Disease, 2016:4:191-200. https://doi.org/10.1002/iid3.105.

The present inventors recognized that application of AEFs to tissue affected by an autoinflammatory disease can be used to treat the autoinflammatory disease because decreased expression of BTNL9 is associated with the autoinflammatory disease, and AEFs increase expression of BTNL9. Applying AEFs to tissue affected by an autoinflammatory disease increases expression of BTNL9 and would inhibit inflammation. In this manner, AEFs can be used to treat autoinflammatory diseases (e.g., Crohn's disease, ulcerative colitis, intestinal inflammation).

AEFs can be applied in a targeted or local manner to cells, or an organ or region of the body containing cells suspected of being in need of increased expression of BTNL9 protein. In this manner, the alternating electrical fields can be locally applied to the cells for a suitable duration and at a suitable frequency, as described herein.

Figure 12:
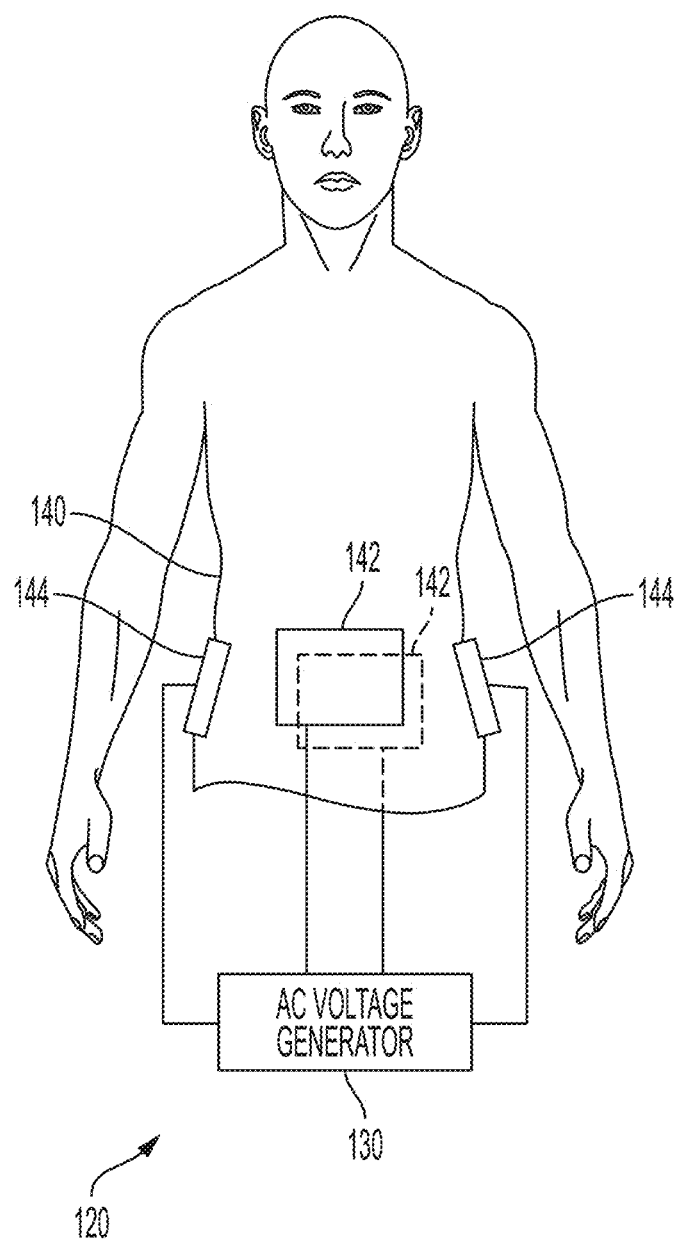
FIG. 12 is a schematic representation of a system for applying alternating electric fields to tissue in a person's abdomen to treat an autoinflammatory disease or mitochondrial disease.

FIG. 12 depicts an example system 120 for applying AEFs to tissue in a person's abdomen that is used to treat tissue (e.g., gastrointestinal) affected by an autoinflammatory disease (e.g., Crohn's disease). The system 120 includes an AC voltage generator 130, a first set of electrodes 144 positioned on the right and left side of the abdomen, and a second set of electrodes 142 positioned on the front and back of the abdomen. Each of the electrodes 142, 144 includes a plurality of elements wired in parallel. In alternative embodiments, elements with different shapes may be used, depending on the anatomical location where the electrodes will be positioned for any given autoinflammatory disease.

To use this system, the first set of electrodes 144 is applied to the subject's body (i.e., on the right and left sides of the abdomen in the illustrated embodiment). The first set of electrodes 144 is positioned with respect to the target region so that application of an AC voltage between the electrodes 144 will impose an alternating electric field with a first orientation (i.e., right to left in the illustrated embodiment) through tissue that is being affected by the autoinflammatory disease in the target region (i.e., the abdomen in the illustrated embodiment). The second set of electrodes 142 is also applied to the subject's body (i.e., on the front and back of the abdomen in the illustrated embodiment). The second set of electrodes is positioned with respect to the target region so that application of an AC voltage between the electrodes 142 will impose an alternating electric field with a second orientation through the tissue (i.e., front to back in the illustrated embodiment). The first orientation and the second orientation are different (and are roughly perpendicular in the illustrated embodiment).

After the first and second set of electrodes 142, 144 have been applied to the subject's body, the AC voltage generator 130 repeats the following steps in an alternating sequence: (a) applying a first AC voltage between the electrodes of the first set 144, such that an alternating electric field with the first orientation is imposed through the tissue and (b) applying a second AC voltage between the electrodes of the second set 142, such that an alternating electric field with the second orientation is imposed through the tissue. The alternating electric field with the first orientation has a frequency and a field strength such that when the alternating electric field with the first orientation is imposed in the tissue, the alternating electric field with the first orientation inhibits inflammation in the tissue. And the alternating electric field with the second orientation has a frequency and a field strength such that when the alternating electric field with the second orientation is imposed in the tissue, the alternating electric field with the second orientation inhibits inflammation in the tissue.

In some embodiments, all the electrodes are positioned on the subject's body (as depicted in FIG. 12); in other embodiments, all the electrodes may be implanted in the subject's body (e.g., just beneath the subject's skin, or in the vicinity of the organ being treated); and in other embodiments, some of the electrodes are positioned on the subject's skin and the rest of the electrodes are implanted in the subject's body.

The same frequency that is used in the Optune® system to treat glioblastoma (i.e., 200 kHz) may also be used to treat an autoinflammatory disease by increasing expression of BTNL9, as described above. But in alternative embodiments, a different frequency may be used. For example, the frequency of the AEFs that are used to treat inflammatory diseases may be between 100 and 300 kHz, between 50 and 500 kHz, or between 25 kHz and 1 MHz. The optimal frequency may be determined experimentally for each individual autoinflammatory disease. Preferably, care is taken to ensure that the AEFs at the selected frequency do not adversely heat portions of the subject's body.

The field strength of the AEFs may be between 0.2 and 1 V/cm RMS, between 1 and 5 V/cm RMS, or between 5 and 25 V/cm RMS. The optimal field strength may be determined experimentally for each individual autoinflammatory disease. Here again, care is preferably taken to ensure that the AEFs at the field strength that is being used do not adversely heat portions of the subject's body.

The orientation of the AEFs may be switched at one second intervals between two different orientations by applying AC voltages between two different sets of electrodes, as done in the Optune® system. But in alternative embodiments, the orientation of the AEFs can be switched at a faster rate (e.g., at intervals between 1 and 1000 ms) or at a slower rate (e.g., at intervals between 1 and 100 seconds). In other alternative embodiments, the electrodes need not be arranged in pairs. See, for example, the electrode positioning described in U.S. Pat. No. 7,565,205, which is incorporated herein by reference. In other alternative embodiments, the orientation of the field need not be switched at all, in which case only a single pair of electrodes is required.

In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body.

Optionally, thermal sensors (not shown) may be included at the electrodes, and the AC voltage generator 130 can be configured to decrease the amplitude of the AC voltages that are applied to the electrodes if the sensed temperature at the electrodes gets too high.

In some embodiments, one or more additional pairs of electrodes may be added and included in the sequence. In other embodiments, the field is only imposed in the target region with a single orientation, in which case the alternating sequence described above may be replaced with a continuous AC signal that is applied to a single set of electrodes (e.g., positioned on opposite sides of the target region).

Note that while FIG. 12 depicts an embodiment in which the AEFs are applied to the abdomen, the AEFs may be applied to different portions of a subject's body as described above in alternative embodiments.

The AEFs may be used to treat an autoinflammatory disease in tissue (e.g., the abdomen of a first person with Crohn's disease) that is tumor free. Alternatively, the AEFs may be used to treat an autoflammatory disease in tissue that contains a tumor (e.g., the abdomen of a different person with both Crohn's disease and a cancer in an organ in the abdomen).

Finally, AEF-based autoinflammatory therapy may optionally be combined with conventional drugs that are used to treat the respective disease.

Part 3-Treatment of Mitochondrial Diseases

Aberrant mitochondrial complex I activation in the pancreas of diabetic patients causes an overflow of NADH that is diverted into ROS (radical oxidative species) production leading to beta-cell dysfunction and death. Wu et al., *Pancreatic mitochondrial complex I exhibits aberrant hyperactivity in diabetes*. Biochem. Biophys. Rep. 11(2017), pp. 119-129. It is believed that this upregulation or hyperactivity is in response to NADH/NAD+ redox imbalance caused by overproduction of NADH by the conventional metabolic pathways. See, e.g., Schapira et al., *Mitochondrial complex I deficiency in Parkinson's disease*, J Neurochem. 1990 Mar;54(3):823-7.

Downregulating mitochondrial complex I (e.g., through application of alternating electrical fields) can, restore NADH/NAD+ redox balance in subjects with mitochondrial disorders related to NADH/NAD+ redox balance.

As shown in FIGS. 11A and 11B, application of alternating electrical fields (e.g., TTFields) at frequencies between 100 and 400 kHz to adult and pediatric glioblastoma brain cells (GBM) results in significant downregulation of MT-ND3, MT-ND5 and MT-ND6, all of which are subunits of the mitochondrial complex I NADH Dehydrogenase.

As shown in FIG. 11A, MT-ND5 is the most downregulated gene in response to exposure to TTFields (FIG. 11A). Downregulation of MT-ND5 mRNA is correlated with downregulation of MT-ND5 protein expression as shown in FIG. 11B where MT-ND5 protein is increased by at least 2-fold following exposure to TTFields for 72 hours at 130 kHz and 200 kHz.

The present inventors recognized that application of AEFs to tissue affected by mitochondrial disorders can be used to treat the mitochondrial disorders because AEFs decrease mitochondrial complex I NADH Dehydrogenase gene (e.g., MT-ND3, MT-ND5 and MT-ND6). Decreased expression of mitochondrial complex I NADH Dehydrogenase genes is associated with restoring NADH/NAD+ balance caused by overproduction of NADH. Applying AEFs to tissue affected by a mitochondrial disorder decreases expression of mitochondrial complex I NADH Dehydrogenase genes, restoring NADH/NAD+ balance and treating mitochondrial disorders (e.g., NAFLD).

In some instances, NADH/NAD+ redox balance in cells of a subject can be restored by applying an alternating electric field having a frequency between 100 and 400 kHz to the cells. In this aspect, application of the alternating electric field is continued until the NADH/NAD+ redox balance in the cells is at least partially restored.

The term "NADH/NAD+ redox balance" refers to an amount of NADH compared to NAD+ in a cell. This balance can indicate whether the metabolic functioning of the cell is normal. An abnormal NADH/NAD+ redox balance in a subject can indicate the subject has a mitochondrial disorder.

In some instances, downregulating complex I (e.g., through application of alternating electrical fields) can, for example, restore NADH/NAD+ redox balance in subjects with conditions or diseases related to NADH/NAD+ redox balance.

In some instances, the alternating electrical field can be applied in a targeted or local manner to cells, or an organ or region of the body containing cells suspected of having a mitochondrial disorder or aberrant NADH/NAD+ redox balance. In this manner, the alternating electrical fields can be locally applied to the cells for a suitable duration and at a suitable frequency, as described herein.

In some instances, the expression level of mitochondrial complex I NADH dehydrogenase subunit proteins is downregulated compared to a subject that is not exposed to the alternating electric fields.

In some instances, the mitochondrial complex I NADH dehydrogenase subunit proteins are selected from the group consisting of MT-ND3, MT-ND5 and MT-ND6. See, e.g., FIGS. 11A and 11B.

In some instances, the expression level of MT-ND5 is downregulated greater than 2-fold compared to a subject that is not exposed to the alternating electric field. See, e.g., FIGS. 11A and 11B.

AEFs can be applied to a subject or patient before, during, or after administering a drug that can be used to treat a mitochondrial disorder. In some instances, at least a portion of the applying is performed after the administering and before the drugs are eliminated from the subject's body.

In some instances, the applying has a duration of at least, for example, 3, 6, 12, 24, 36 or 72 hours. The application of the electrical field for a given time period may be accomplished in a single interval. Alternatively, the application of the electrical field could be interrupted by breaks. For example, 6 sessions with a duration of 12 hours each, with a 2 hour break between sessions. The term "break" refers to an interval of time where the electrical field is not applied.

In some instances, one or more drugs are administered at therapeutically effective doses, and the alternating electric field has a field strength of at least 1 V/cm in at least a portion of the target region. In some of these instances, the applying has a duration of at least 3, 6, 12, 24, 36 or 72 hours.

The MT-ND5 gene encodes the NADH-ubiquinone oxidoreductase chain 5 protein (NAD5) and has been implicated in mitochondrial disorders related to NADH/NAD+ redox.

NAFLD is the most common cause of liver disease in the Western world, encompassing the spectrum of liver diseases, including simple steatosis, nonalcoholic steatohepatitis, cirrhosis, liver failure, and hepatocellular carcinoma. Consequently, a set of metabolic adaptations supervene, such as increased β oxidation. This adaptation induces metabolic inflexibility, and drives the oxidative stress and mitochondrial dysfunction that are apparent in NAFLD. Elhassan et al., Targeting NAD+ in Metabolic Disease: New Insights Into an Old Molecule, Journal of the Endocrine Society, Volume 1, Issue 7, 1 July 2017, Pages 816-835, https://doi.org/10.1210/js.2017-00092. It has been previously shown that highly expressed MT-ND3 positively associated with severity of hepatic steatosis, a stage in progression of NAFLD. Wang et al., APMIS. Highly expressed MT-ND3 positively associated with histological severity of hepatic steatosis, 2014 May;122(5):443-51 doi: 10.1111/apm.12166. Epub 2013 September 11.

FIG. 12 depicts an example system 120 for applying AEFs to tissue in a person's abdomen that is used to treat a mitochondrial disorder (e.g., NAFLD). The system 120 includes an AC voltage generator 130, a first set of electrodes 144 positioned on the right and left side of the abdomen, and a second set of electrodes 142 positioned on the front and back of the abdomen. Each of the electrodes 142, 144 includes a plurality of elements wired in parallel. In alternative embodiments, elements with different shapes may be used, depending on the anatomical location where the electrodes will be positioned for any given mitochondrial disorder.

To use this system, the first set of electrodes 144 is applied to the subject's body (i.e., on the right and left sides of the abdomen in the illustrated embodiment). The first set of electrodes 144 is positioned with respect to the target region so that application of an AC voltage between the electrodes 144 will impose an alternating electric field with a first orientation (i.e., right to left in the illustrated embodiment) through tissue that is being affected by the mitochondrial disorder in the target region (i.e., the abdomen in the illustrated embodiment). The second set of electrodes 142 is also applied to the subject's body (i.e., on the front and back of the abdomen in the illustrated embodiment). The second set of electrodes is positioned with respect to the target region so that application of an AC voltage between the electrodes 142 will impose an alternating electric field with a second orientation through the tissue (i.e., front to back in the illustrated embodiment). The first orientation and the second orientation are different (and are roughly perpendicular in the illustrated embodiment).

After the first and second set of electrodes 142, 144 have been applied to the subject's body, the AC voltage generator 130 repeats the following steps in an alternating sequence: (a) applying a first AC voltage between the electrodes of the first set 144, such that an alternating electric field with the first orientation is imposed through the tissue and (b) applying a second AC voltage between the electrodes of the second set 142, such that an alternating electric field with the second orientation is imposed through the tissue. The alternating electric field with the first orientation has a frequency and a field strength such that when the alternating electric field with the first orientation is imposed in the tissue, the alternating electric field with the first orientation treats the mitochondrial disorder. And the alternating electric field with the second orientation has a frequency and a field strength such that when the alternating electric field with the second orientation is imposed in the tissue, the alternating electric field with the second orientation treats the mitochondrial disorder.

In some embodiments, all the electrodes are positioned on the subject's body (as depicted in FIG. 12); in other embodiments, all the electrodes may be implanted in the subject's body (e.g., just beneath the subject's skin, or in the vicinity of the organ being treated); and in other embodiments, some of the electrodes are positioned on the subject's skin and the rest of the electrodes are implanted in the subject's body.

The same frequency that is used in the Optune® system to treat glioblastoma (i.e., 200 kHz) may also be used to treat an mitochondrial disorder by decreasing expression of MT-ND3, MT-NDS, or MT-ND6, as described above. But in alternative embodiments, a different frequency may be used. For example, the frequency of the AEFs that are used to treat the mitochondrial disorder may be between 100 and 300 kHz, between 50 and 500 kHz, or between 25 kHz and 1 MHz. The optimal frequency may be determined experimentally for each individual mitochondrial disorder. Preferably, care is taken to ensure that the AEFs at the selected frequency do not adversely heat portions of the subject's body.

The field strength of the AEFs may be between 0.2 and 1 V/cm RMS, between 1 and 5 V/cm RMS, or between 5 and 25 V/cm RMS. The optimal field strength may be determined experimentally for each individual mitochondrial disorder. Here again, care is preferably taken to ensure that the AEFs at the field strength that is being used do not adversely heat portions of the subject's body.

The orientation of the AEFs may be switched at one second intervals between two different orientations by applying AC voltages between two different sets of electrodes, as done in the Optune® system. But in alternative embodiments, the orientation of the AEFs can be switched at a faster rate (e.g., at intervals between 1 and 1000 ms) or at a slower rate (e.g., at intervals between 1 and 100 seconds). In other alternative embodiments, the electrodes need not be arranged in pairs. See, for example, the electrode positioning described in U.S. Pat. No. 7,565,205, which is incorporated herein by reference. In other alternative embodiments, the orientation of the field need not be switched at all, in which case only a single pair of electrodes is required.

In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body.

Optionally, thermal sensors (not shown) may be included at the electrodes, and the AC voltage generator 130 can be configured to decrease the amplitude of the AC voltages that are applied to the electrodes if the sensed temperature at the electrodes gets too high.

In some embodiments, one or more additional pairs of electrodes may be added and included in the sequence. In other embodiments, the field is only imposed in the target region with a single orientation, in which case the alternating sequence described above may be replaced with a continuous AC signal that is applied to a single set of electrodes (e.g., positioned on opposite sides of the target region).

Note that while FIG. 12 depicts an embodiment in which the AEFs are applied to the abdomen, the AEFs may be applied to different portions of a subject's body as described above in alternative embodiments.

The AEFs may be used to treat a mitochondrial disorder in tissue (e.g., the liver of a first person with NAFLD) that is tumor free. Alternatively, the AEFs may be used to treat a mitochondrial disorder in tissue that contains a tumor (e.g., the liver of a different person with both NAFLD and liver cancer).

Finally, AEF-based mitochondrial disorder therapy may optionally be combined with conventional drugs that are used to treat the respective disease.

Genome Wide Expression and Anti-proliferative Effect of TTFields Therapy on Pediatric and Adult Brain Tumors The scarcity of effective treatment options for high grade brain tumors has led to a wide ranging search for alternative means of therapy for these difficult to treat tumors. Electrical field therapy is one such area that has been considered. The Optune system is an FDA approved novel anti-mitotic device that delivers continuous alternating electric fields to the patient for the treatment of primary and recurrent Glioblastoma multiforme (GBM) (tumor treating fields—TTFields). Alternative electric fields delivery systems are also being investigated for the treatment of various cancers. Aspects described herein provide the first study of genome wide expression of electrotherapy on brain tumor cell lines. In vitro evidence is also provided for the potential of using Optune electric fields for the treatment of pediatric brain tumors.

Methods

A variety of high-grade adult and pediatric brain tumor cell lines were treated with TTFields. The effects of electric fields were assessed through a number of avenues including; viability, gene expression (Clariom S array), cell cycle, and combinational effects with chemotherapies.

Chemotherapeutic Combinations

Cells were treated with TMZ (Sigma-Aldrich), Paclitaxel (Sigma-Aldrich) and Mebendazole (Sigma-Aldrich) as a monotherapy or in combination with TTFields. Each of the drugs were administered at their IC50 (high dose) or 10% IC50 (low dose), with the IC50s being determined through drug-response curves. The IC50 of Paclitaxel (0.36-4.6 nM) and Mebendazole (0.03-1.2 μM) was established (FIG. 5C) and then the higher dose (IC50) and a lower dose (IC50/10) was used on the indicated cell lines.

Results

TTFields significantly affected brain tumor cell line viability, with TTFields promoting G2-phase accumulation. TTFields can be used, for example, to augment the efficacy of Temozolomide, Paclitaxel and Mebendazole. Lastly, genome-wide expression assessment suggesting novel interactions with electrical treatment and endoplasmic reticulum and mitochondrial functioning—promoting endoplasmic reticulum stress.

Conclusions

Efficacy of TTFields against pediatric high-grade brain tumors has been demonstrated. Multiple mechanisms of action have been elucidated while providing novel avenues for future research.

Introduction

Glioblastoma multiforme (GBM) is the most common and aggressive adult primary brain tumor (Schwartzbaum et al., 2006). The current standard of care is radical surgical resection along with chemoradiation therapy with temozolomide (TMZ) (Stupp et al., 2005). Despite decades of advancement in the laboratory with regards to potential treatments, little progress has been made in the clinic as GBM is still an exceptionally poor prognosis tumor. More recently, there is growing pre-clinical (Xu et al., 2016, Sebastiano et al., 2018, Giladi et al., 2017, Gera et al., 2015) and clinical (Stupp et al., 2017, Stupp et al., 2012a) data suggesting that electric fields may present an effective treatment modality for high-grade brain tumor patients. It is proposed in the existing data that electric fields may function through perturbation of polarized cytokinetic proteins (Gera et al., 2015, Kirson et al., 2004), disruption in membrane permeability (Xu et al., 2016) and promoting autophagy (Shteingauz et al., 2018), but further emerging mechanisms are currently being elucidated.

Recent work has demonstrated that glioma cells rely on functional synaptic connections with both neurons and other tumor cells (Venkataramani et al Nature 2019 and Venkatesh et al Nature 2019). Potassium currents evoked by these electrical mechanisms form an intra-tumoral electrical network and blocking this network pharmacologically can limit glioma growth. This work highlights the importance of electrophysiology and its manipulation (potentially by exogenous current from systems such as Optune) may hold promise as a therapeutic avenue for treating these incurable cancers. The exact mechanism for the effects of electrical fields on cancer cells has implications for the future development and optimization of this emerging therapeutic modality.

At present, the only electrotherapy approved for adult GBM is the Optune™ system (Novocure Inc.). The system includes a portable electric field generator which delivers low intensity (1-3V/cm), intermediate frequency (200 kHz), alternating electric fields—termed 'Tumor Treating Fields' (TTFields) (Kirson et al., 2004, Stupp et al., 2017). The TTFields are delivered to the patient's brain via external electrode arrays adhered to the scalp. TTFields therapy has been evaluated in multiple phase III trials, although some criticisms have been made of trial design (Wick, 2016). Published studies suggest benefit to both recurrent (Stupp et al., 2012a) and primary GBM patients (Stupp et al., 2017). Concerns have been raised regarding therapeutically relevant intensities of TTFields at the initial tumor site (Korshoej et al., 2018), coupled with the very significant local recurrence patterns of GBM tumors (Rapp et al., 2017). Other suggested electrotherapy strategies for localized delivery of electric fields, include Intratumoral Modulation Therapy (IMT) (Xu et al., 2016, Sebastiano et al., 2018).

Development of internalized electrotherapies seek to exploit the electrosensitivity of tumor cells while overcoming limitations of delivery from an external system (Chaudhry et al., 2015, Benson, 2018), as well as overcoming concerns of cost of the TTFields therapy (Bernard-Arnoux et al., 2016). Xu and colleagues (Xu et al., 2016) described their preliminary in vitro IMT investigation, with their key finding being; 4V/130 Hz electric fields induced apoptosis in primary GBM cells, have no notable effect on primary neurons, and efficacy may be improved with the addition of TMZ (Xu et al., 2016). More recently, the IMT approach was altered to deliver 200 kHz electric fields in in vitro and in vivo models (Sebastiano et al., 2018). The main findings of this study were in line with the previous reports, demonstrating efficacy against GBM cells while not affecting primary neurons, as well showing greater efficacy when combined with TMZ. Notably, the study also demonstrated safety of IMT in vivo as well as significant reductions in tumor volume across their pilot 15-animal cohort study (Sebastiano et al., 2018).

These experiments examine the effects of TTFields on pediatric brain tumor cell lines. Electric fields treatments of varying intensities and frequencies delivered by Optune significantly affect primary and commercial brain tumor cell line viability and cell cycling, while not affecting viability of non-dividing astrocyte cells. The efficacy of electric fields, including the clinically relevant Optune TTF, may be improved with the addition of TMZ and mitotic inhibitors. Genome-wide expression analysis of electric fields treated GBM cells examine the genetic effects of electrical field treatments on tumor cells, giving further suggestions to possible mechanisms of action.

Materials and Methods

Cell Culture and Cell Lines

GIN-28, GIN-31 and GCE-77 cells (Patient derived primary low passage GBM lines) were grown in DMEM (Gibco™) supplemented with 15% FBS. U87-MG (Adult GBM) cells were grown in DMEM (Gibco™) supplemented with 10% foetal bovine serum (FBS). KNS42 and SF188 (Pediatric GBM) cells were grown in DMEM/F-12 (Gibco™) supplemented with 10% FBS and 1% L-glutamine. DKFZ-EPN1 and BXD-1245-EPN (Pediatric Ependymoma) cells were grown in DMEM supplemented with 10% FBS. DAOY (SHH Medulloblastoma) cells were grown in MEM (Sigma-Aldrich) supplemented with 10% FBS, 1% L-Glutamine, and 1% Sodium Pyruvate. UW228-3 (SHH Medulloblastoma) cells were grown in DMEM/F-12 supplemented with 10% FBS. Neural stem cells and post-mitotic astrocytes were derived from human induced pluripotent stem cells and grown as described by (Julia et al., 2017). All cells were maintained at 37° C. in a $CO_2$ incubator and have been STR genotyped to ensure correct identification and, in the case of the primary low passage cell lines, that they maintain the same genetic profile as their parent tumor over multiple passages.

TTFields Application

TTFields were applied using the Inovitro™ system (Novocure, Haifa). The system consists of two pairs of perpendicular transducer arrays on the outer walls of a ceramic Petri dish. A sinusoidal waveform generator was attached to the transducer arrays to produce alternating electric fields at frequencies between 100-400 kHz and 1.75V/cm intensity. The electric fields alternated orientation of 90° every second. The temperature was measured to be 37° C. inside the dishes by 2 thermistors attached to the ceramic walls.

Intensity and Frequency Titration

Cell Viability Assay

PrestoBlue™ was added to each sample at a time-point at a 1:10 dilution. Samples were incubated at 37° C. for 30 minutes. 100 µl (triplicate) of the PrestoBlue solution was transferred to a black-bottomed 96-well plate and fluorescence was analyzed via UV-Vis Spectroscopy at excitation/emission wavelengths at 560/590 nm with the FLUOstar Omega (BMG Labtech).

Gene Expression Analysis

Human Clariom™ S Arrays (ThermoFisher™) were used for an unbiased, whole transcriptome gene expression analysis of Inovitro treated GBM cell lines. Microarray processing was performed by Dr. Marcos Castellenos and Dr. Iqbal Khan of Nottingham Arabidopsis Stock Centre (NASC), University of Nottingham.

Gene Expression Data Processing

Hierarchical clustering analyses were performed using Partek®. The criteria of significant genes were; false discovery rate (Bonferroni Correction) and p-value of <0.05, and a fold-change of <−2.0 and >2.0. An unsupervised clustering method was used and analyses were displayed as heatmaps on a genome-wide scale within each electrical treatment. Gene Ontology and KEGG pathway analyses were performed using Enrichr (Chen et al., 2013, Kuleshov et al., 2016). Enrichr was used at http://amp-.pharm.mssm.edu/Enrichr/. The KEGG Pathways were generated from the gene target lists of commonly differentially expressed genes between the cell lines and treatments (See, e.g., FIGS. 8A-8B, 9A-9B, and 10A-10B and https://www.genomejp/kegg/kegg2.html).

Western Blot

Cell pellets were collected following electric fields treatment and then treated with protease cocktail buffer on ice before centrifugation at 13,000× g for 30 minutes. Protein lysates were then retrieved and quantified via Bradford assay. 20 µg of each protein sample was separated on a 10% acrylamide gel and transferred via electrophoresis to nitrocellulose membranes. The membranes were blocked and then incubated at 40 C overnight with the primary antibodies; MT-ND5 (Abcam), CTSB (Abcam) BTNL9 (Abcam) and GAPDH 1:10,000 (Abcam). Membranes were washed and then incubated at room temperature for 1 hour with complimentary secondary antibodies. Membranes were washed and then incubated in enhanced chemiluminescence and western blotting detection solutions before western blot images being developed.

Results

Figure 2A:
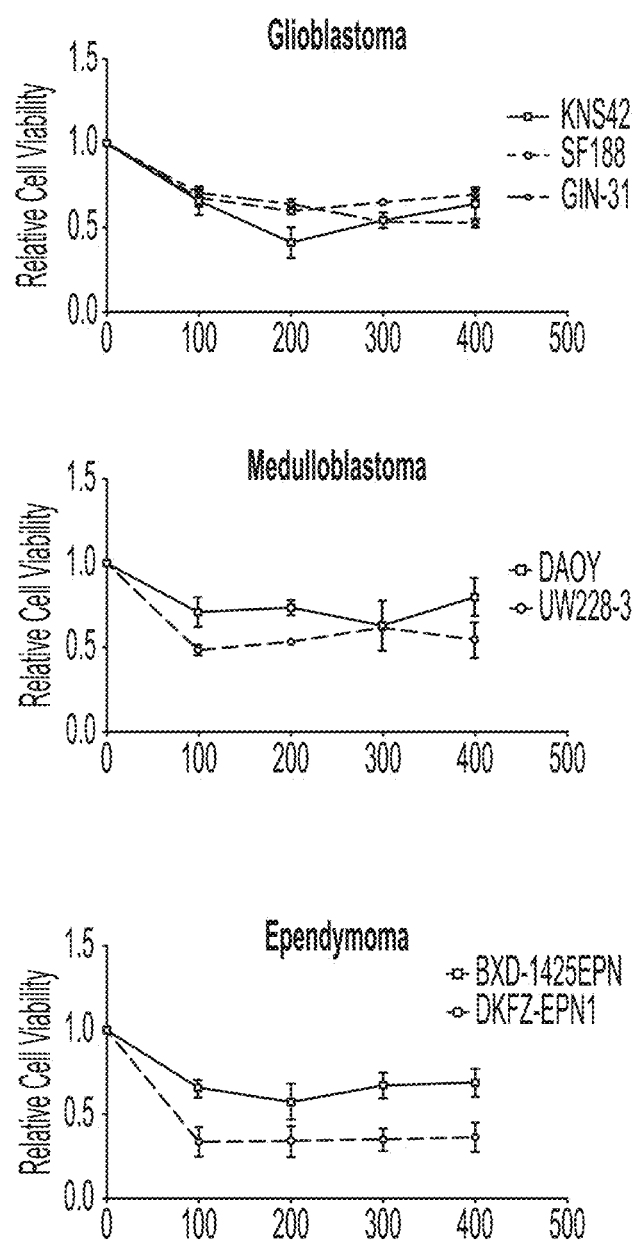
FIG. 2A shows exemplary results of experiments measuring cell viability after treatment with TTFields for 72 hours.
Figure 2B:
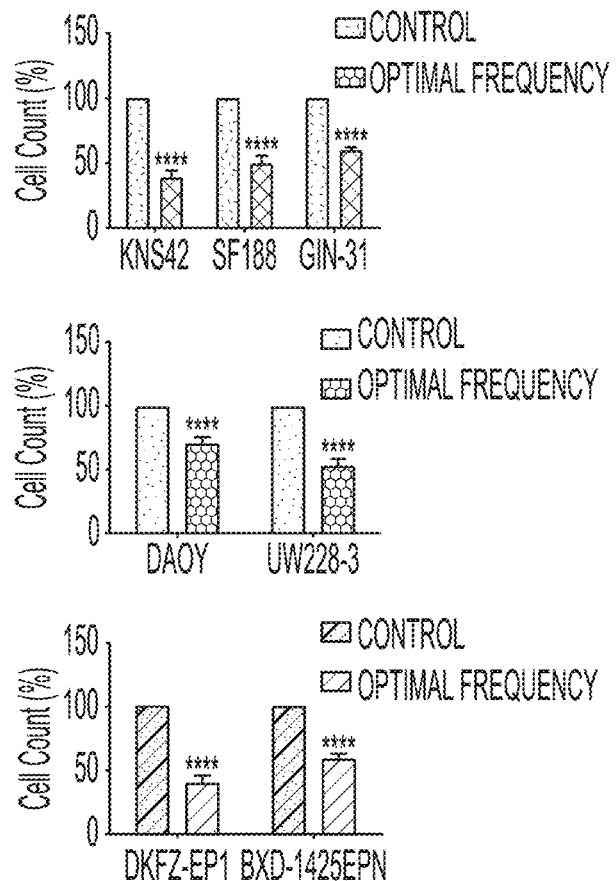
FIG. 2B shows exemplary results of experiments measuring cell viability after treatment with TTFields for 72 hours.

Tumor Treating Fields Demonstrate Variable Efficacy in a Frequency Dependent Manner The optimum frequency of TTFields for the indicated cell lines over a panel of frequencies was determined. TTFields have been tested in various cancer cell lines within 100-500 kHz range (Kirson et al., 2007), and thus far, TTFields have been used clinically on adult GBM patients at a frequency of 200 kHz (Stupp et al., 2017). A panel of pediatric GBM, Medulloblastoma and Ependymoma cell lines, and a primary adult invasive margin GBM cell line was analyzed over a 100-400 kHz range for a 72 hour treatment. Cell viability was measured via Presto Blue, and the relation to Presto Blue to cell viability was validated through cell counts. The cell lines were sensitive to TTFields treatment across the frequencies tested. The GBM cell lines, KNS42, SF188, and GIN-31 had an optimal frequency of 200 kHz, 400 kHz, and 200 kHz, respectively, while experiencing a reduction of 61%, 50%, and 40% cell count (p=<0.0001; t-test). The Medulloblastoma cell lines, DAOY and UW228-3, had an optimal frequency of 300 kHz and 100 kHz, with reduction of 30% and 47% in the cell counts (p=<0.0001; t-test). Lastly, the Ependymoma cell lines tested, DKFZ-EPN1 and BXD-1425EPN, had optimal frequencies of 100 kHz and 200 kHz, with reductions of cell counts of 60% and 40% (p=<0.0001; t-test). The cell lines had varying responses to TTFields as a treatment, as well as with response to different frequencies, it appeared that the Ependymoma cell lines had the most similar responses to the frequencies used. Interestingly, the pediatric GBM cell line SF188 was determined to have an optimal frequency of 400 kHz as opposed to the accepted 200 kHz for adult GBM in the clinic, however, KNS42 cells were most affected by TTFields at 200 kHz (FIG. 2).

Figure 2C:
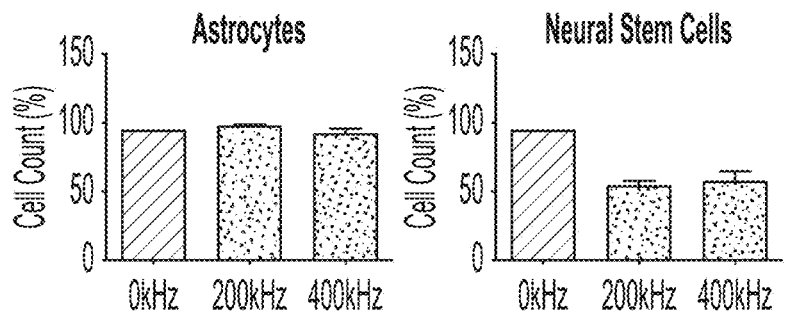
FIG. 2C shows exemplary results of experiments measuring cell viability of human neural stem cells and astrocytes cell lines treated for 72 hours with TTFields at 200 kHz and 400 kHz.

The efficacy of TTFields treatment was confirmed by treating the cell lines for 72 hours at 200 kHz and 400 kHz TTFields, followed by a Presto Blue assay for assessment of cell viability and a cell count relative to the control cells. Cell counts confirmed the hypothesis that TTFields would only negatively affect the actively dividing cells. The reduction of human neural stem cell counts following TTFields treatment were 41% and 37% (p=0.0018 and p=0.0024; t-test) following treatment with 200 kHz and 400 kHz TTFields, respectively. There were no significant differences between the 200 kHz and 400 kHz treatments (FIG. 2C). These results are consistent with previous literature regarding TTFields having no efficacy against non-dividing cells (Xu et al., 2016, Sebastiano et al., 2018, Kirson et al., 2004, Jo et al., 2018).

Figure 3A:
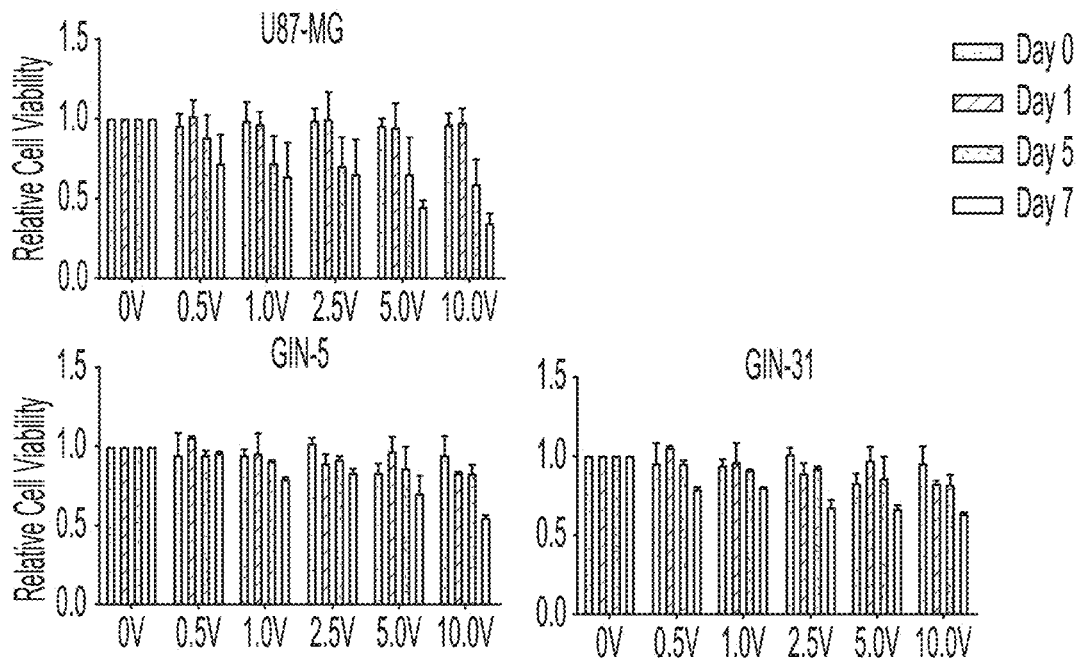
FIG. 3A shows exemplary results of experiments measuring cell viability of U87-MG, KNS42, GIN-5, and GIN-31 cells lines over a seven day time course at various field strengths.
Figure 3B:
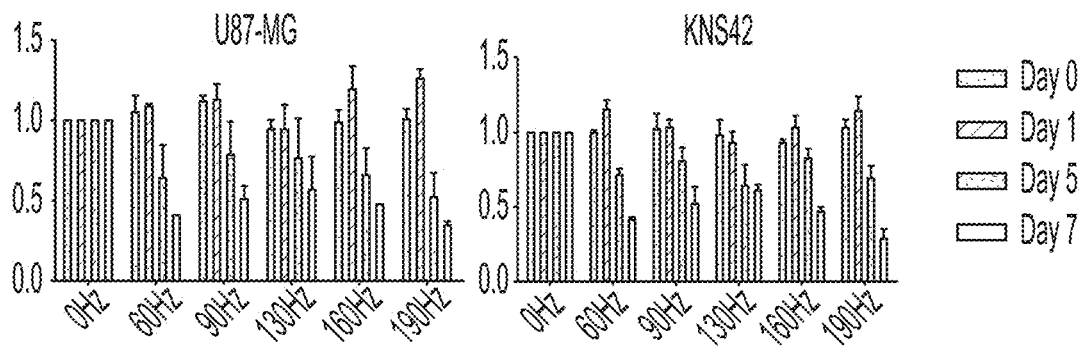
FIG. 3B shows exemplary results of experiments measuring cell viability at various frequencies.
Figure 3C:
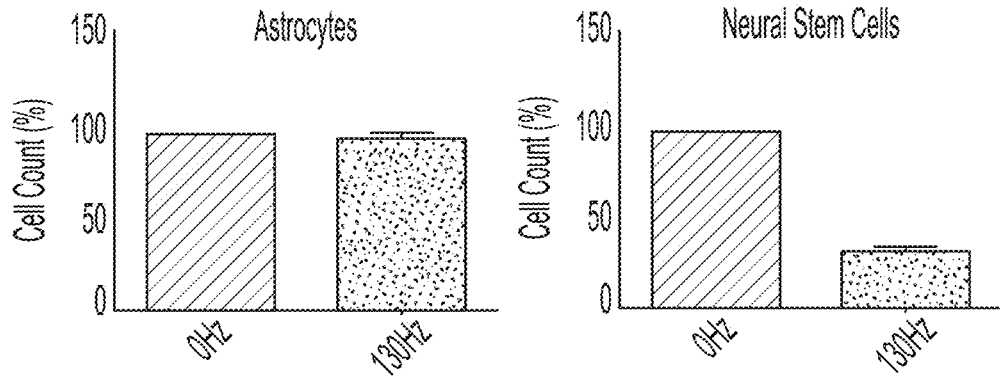
FIG. 3C show exemplary results of experiments measuring cell viability in astrocytes (left panel) and neural stem cells (right panel) at 0 Hz and 130 Hz.

Electric Fields Perturb Cell Cycling of Brain Tumor Cell Lines in a Frequency Dependent Manner TTFields have previously been shown to promote G2/M-phase accumulation through interactions with tubulin dynamics (Kirson et al., 2004, Giladi et al., 2015, Gera et al., 2015). The panel of pediatric brain tumor cell lines were treated with TTFields for 72 hours at their optimal frequencies, and their cell cycling was analysed using PI staining and flow cytometry. The results are consistent with previous data (Silginer et al., 2017), TTFields treatment caused G2/M-phase accumulation for all cell lines; with an increase of 9% and 11% (p=0.0297 and p=0.0037; two-way ANOVA) for KNS42 and SF188 cell lines, 11% and 12% (p=<0.0001; two-way ANOVA) for DAOY and UW228-3 cell lines, and 13% and 8% (p=0.0040 and p=0.0024; two-way ANOVA) for BXD-1425EPN and DKFZ-EPN1 cell lines, respectively. The cell lines; DAOY, UW228-3, and DKFZ-EPN1 also had significant G0-phase depletion; 8%, 7%, and 7% (p=0.0002, p=<0.0001 and p=0.0057; two-way ANOVA), respectively. These cell lines also experienced a slight S-phase accumulation as well; 6%, 4%, and 10% (p=0.0131, p=<0.0001 and p=<0.0001; two-way ANOVA). None of the cell lines had significant levels of subG0-phase accumulation, suggesting that TTFields has a predominantly cytostatic over a cytotoxic effect in our tested pediatric brain tumor cell lines (FIG. 3).

The Efficacy of Electric Fields may be Increased with the Addition of Chemotherapies in Brain Tumor Cell Lines As these data suggest that TTFields targets the G2/M-phase of the cell cycle, this phase was further targeted with the tubulin-interacting mitotic inhibitors, Paclitaxel and Mebendazole. This strategy of targeting the same region of the cell cycle with different therapies seeks to overcome the axis-dependent nature of TTFields which may limit efficacy of the treatment. The IC50 of Paclitaxel (0.4-4.6 nM) and Mebendazole (0.02-1.2 µM) (FIG. 5) was established with respect to the brain tumor cell lines. A lower and a higher dose was used to treat the cell lines as a monotherapy and in combination with TTFields for a 72 hour treatment for comparison. The cell lines were sensitive to the mitotic inhibitors used, with reductions of cell viability of 30% and 39% (p=0.0034 and p=<0.0001; two-way ANOVA) for SF188 cells, 32% and 28% (p=<0.0001; two-way ANOVA) for UW228-3 cells, and 23% and 30% (p=<0.0001; two-way ANOVA) for BXD-1425EPN cells, for Paclitaxel and Mebendazole, respectively.

The lower and higher doses of Paclitaxel in combination with TTFields treatment at the determined optimal frequency were compared to Paclitaxel-treated cells alone. Reductions in cell viability were recorded in SF188 cells at 37% and 33% (p=<0.0002 and p=0.0006, two-way ANOVA), UW228-3 cells at 34% and 22% (p=<0.0001 and p=0.0012, two-way ANOVA) and BXD-1425EPN cells at 27% and 34% (p=<0.0001, two-way ANOVA) (FIG. 4A). TTFields was also combined with the mitotic inhibitor, Mebendazole. The lower and higher doses of Mebendazole in combination with TTFields treatment at the determined optimal frequency were compared to Mebendazole-treated cells alone. Reductions in cell viability were recorded in SF188 cells at 40% and 22% (p=<0.0001 and p=0.0092, two-way ANOVA), UW228-3 cells at 25% and 29% (p=<0.0001 and p=0.0012, two-way ANOVA) and BXD-1425EPN cells at 19% and 16% (p=<0.0001, two-way ANOVA) (FIG. 3B). Overall, our pediatric brain tumor cell lines were more significantly affected by the combinational approach. The additive effect of TTFields to mitotic inhibitors in the cell lines is consistent with previous reports in multiple cell lines with varying responses to TTFields (Voloshin et al., 2016).

Electric Fields Treatments Cause Gene Expression Changes in GBM Cell Lines

Discussion

Optune exhibits efficacy against adult and pediatric brain tumor cell lines in vitro, and this efficacy increased with optimization of frequency and other parameters.

TTFields treatment efficacy was increased through manipulation of the frequency between 100 kHz and 400 kHz. The effects of manipulating the intensity of TTFields was not explored as this has already been established in vitro (Porat et al., 2017). TTFields in the range of 100-400 kHz over a 72 hour treatment period demonstrated efficacy across all tested cell lines, consistent with data suggesting efficacy against actively dividing cells regardless of cell type (Kirson et al., 2004, Kirson et al., 2009, Porat et al., 2017). It has also been observed that the optimal frequency determined for cell lines is consistent for tumors of the same origin (Porat et al., 2017). However, the cell lines examined herein each have an optimal frequency despite being of the same tumor type, apart from our Ependymoma cell lines which more interestingly appear to be equally influenced throughout the whole range of 100-400 kHz TTFields. There was a variable optimal frequency for the panel of GBM cell lines examined herein, Adult primary cell line (GIN-31) and pediatric cell line (KNS42) had an optimal frequency of 200 kHz—which is consistent with the frequency used in the clinic for adult GBM patients (Stupp et al., 2012b, Stupp et al., 2017). Pediatric cell line (SF188) had an optimal frequency of 400 kHz. These data highlight the need for further development of, for example, strategies for patient optimization of TTFields treatment. Lastly, observations of the optimal frequencies and their corresponding cell type's cell size aligns with the hypothesis that the optimal frequency is inversely proportional to the cell size (Wenger et al., 2018, Kirson et al., 2007). However, both Ependymoma cell lines appeared to be equally affected by all frequencies despite being highly varied in their cell morphology and cell size.

Previous reports have hypothesized that an actively dividing cell is the target of electric field treatment (Kirson et al., 2004), and few reports have shown how these treatments have little to no efficacy on non-dividing cells (Xu et al., 2016, Sebastiano et al., 2018, Kirson et al., 2004, Jo et al., 2018). Our data demonstrates TTFields treatment at 200 kHz and 400 kHz had no effect on cell viability on post-mitotic astrocytes derived from neural stem cells, whereas the treatment still had significant effect on the dividing neural stem cell line.

As described herein, TTFields cause significant shifts in cell cycle phase accumulations TTFields treatments promoting G2/M-phase accumulation in brain tumor cell lines. The accumulation of TTFields treated cells in the G2/M phase has been observed in many different cell lines and tumor types, and has been attributed to perturbation of key mitotic proteins e.g. tubulin and Septin proteins (Giladi et al., 2015, Gera et al., 2015). A number of mitotic proteins have been investigated, however, many proteins may be influenced by an alternating electric field if there is sufficient current and the protein has a sufficiently high dipole moment (Gera et al., 2015). Interestingly, none of the panel of brain tumor cell lines examined herein underwent significant levels of apoptosis, which is consistent with other reports of TTFields not inducing significant apoptosis in glioma models (Silginer et al., 2017, Kessler et al., 2018). The mechanisms by which each cell type evades apoptosis is subject to further investigation.

TTFields combined with TMZ has been shown to increase efficacy irrespective of MGMT status in vitro (Clark et al., 2016) and in vivo (Stupp et al., 2017). The combination of electric fields to chemotherapies, especially with those with limited efficacy against certain patient subgroups, offers a clinical strategy whereby an additional potentially efficacious therapy may be administered without overlapping or significant toxicities (Stupp et al., 2012b, Stupp et al., 2017).

Electric Fields Treatments Cause Gene Expression Changes in GBM Cell Lines

To further explore alternative potential mechanisms of electric fields as a whole, Optune-treated and control untreated KNS42 and GIN-31 cell lines were analyzed using Clariom™ S Human Assays to produce genome-wide expression data. Hierarchical clustering analysis showed differential expression profiles of the examined cell lines. TTFields treatment caused differential expression of 4,746 and 5,500 genes for KNS42 and GIN-31 cells, respectively, with 3,469 commonly differentially expressed genes (FIG. 11A).

Gene ontology analysis implicated that the commonly differentially expressed genes were related to genes involved in mitochondrial and ER functioning; including, electron transport, metabolism, ion signaling and protein folding. It is worth noting that all of these associated genes are significantly downregulated, implying that these processes are also downregulated. Furthermore, KEGG pathway analysis demonstrated significant over-representation of genes known to be involved in the Parkinson, Alzheimer, and Huntington disease pathways in our data (FIGS. 8A-8B, 9A-9B, and 10A-10B). Although these diseases have their own pathologies, they share similarities with regards to their causative factors (Lin and Beal, 2006). All three of the aforementioned diseases have been shown to have significant downregulation of NADH Dehydrogenase, among other oxidative phosphorylation complexes, and we observed significant downregulation of MT-ND3, MT-ND5 and MT-ND6 (subunits of the NADH Dehydrogenase (Bai et al., 2000)) in our cell lines following electrical treatment.

A correlation between MT-ND5, CTSB and BTNL9 gene expression and protein expression was validated via western blot. MT-ND5 was the most downregulated gene (>-100-fold downregulation) and BTNL9 was the only upregulated gene of the top 50 target genes. A western blot confirmed that the expression patterns observed with the gene expression data translated to the changes at the protein level (FIG. 11B).

A significant number of the affected genes in TTFields-treated cells and pathways were associated with mitochondrial and endoplasmic reticulum functioning synonymous with the unfolded protein and the ER stress response. The downregulation of mitochondrial and ER functioning may potentially be a result of the prolonged mitotic arrest from the electrical treatment. Studies have shown where it has that prolonged TTFields exposure may promote ER stress (Shteingauz et al., 2018). Furthermore, the pathway proposed by Shteingauz and colleagues described ATP (Adenosine triphosphate) depletion also being a product of TTFields exposure (Shteingauz et al., 2018). ATP production through metabolic pathways, such as glycolysis and the citric acid cycle, is reliant upon reduction of NAD+ to NADH (Nicotinamide Adenine Dinucleotide) (Jang et al., 2013). This redox process of donating and accepting electrons is reliant upon the electron transport chain, and therefore, it may also be potentially a novel mechanism of electric fields treatments on GBM cell lines. The gene expression analysis provides novel target genes and pathways for TTFields treatment in combination with drugs.

FIG. 2 illustrates the impact of manipulations of frequency (kHz) on the viability of GBM, Medulloblastoma and Ependymoma cell lines. A) Cell lines were treated for 72 hours over a range of frequencies with the Inovitro, with metabolic measurements being taken at the 72 hours end-points. Each cell line demonstrates variable efficacy to TTFields treatment, with no clear pattern of a most optimal frequency for each tumor type tested. B) Cell lines were treated for 72 hours at their determined most efficacious frequency (FIG. 1A) with the Inovitro, with cell counts being taken at 72 hours time-points. Each cell line was significantly affected by TTFields, with variability in efficacy being present between cell lines and tumor types. C) Human neural stem cells and astrocytes cell lines were treated for 72 hours at 200 kHz and 400 kHz TTFields with the Inovitro, with cell counts being taken at the 72 hours end-point. The actively dividing neural stem cells were significantly affected by the electric fields, while the non-dividing astrocytes were not affected by either treatments.

FIG. 3 shows the exemplary impact of electric fields on the cell cycle of brain tumor cell lines. B) Cell lines were treated for 72 hours at the determined optimal frequency TTFields with the Inovitro, with flow cytometry being performed with PI staining to assess cell cycling. The effects of TTFields treatments were different between cell lines, but the most common response of treatment was significant accumulation of cells in the G2-phase and S-phase, and minimal accumulation of cells in the subG0-phase.

Figure 4:
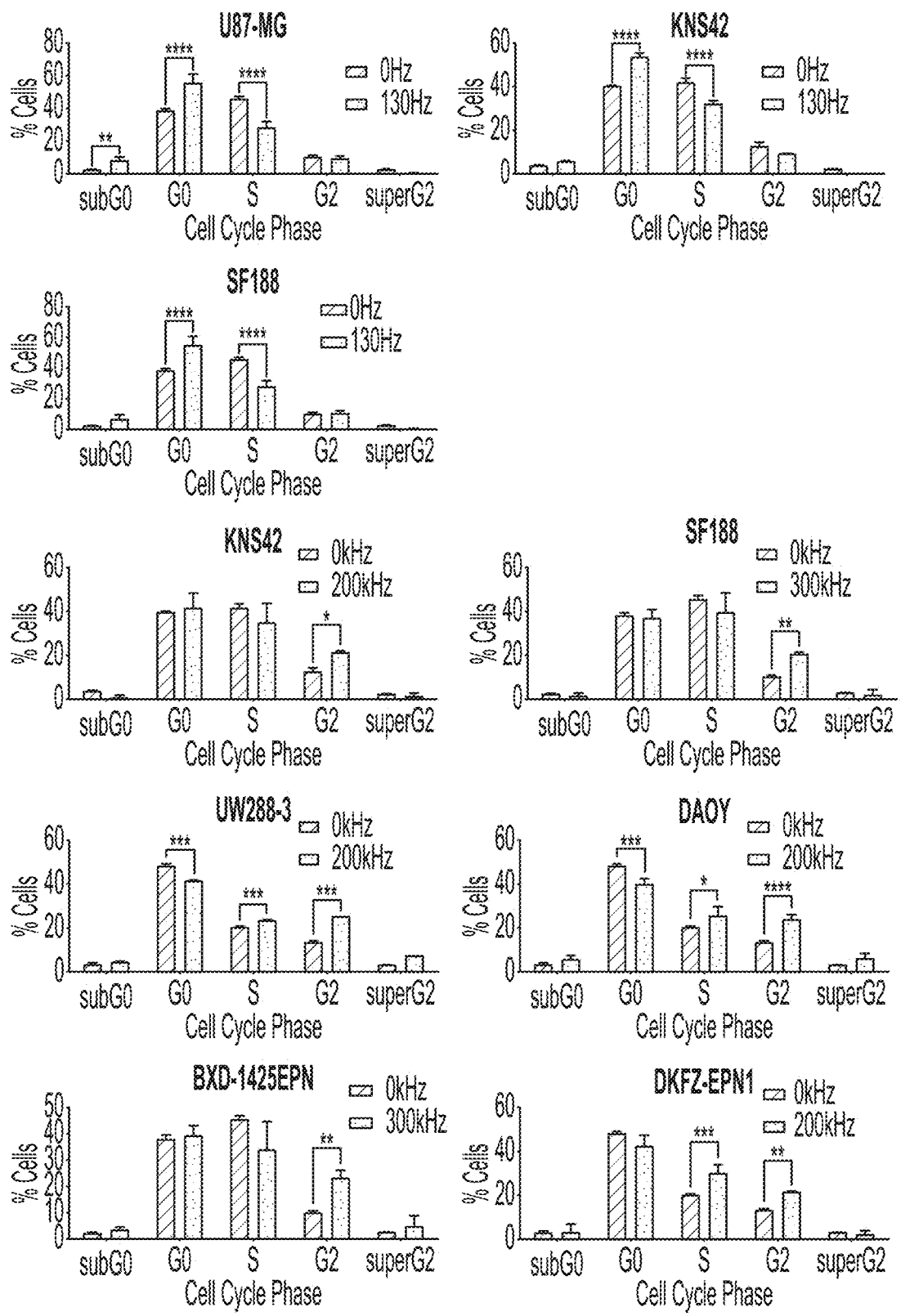
FIG. 4 shows exemplary results of experiments measuring cell viability at the indicated phases of the cell cycle in various brain tumor cell lines.

FIG. 4 shows exemplary results of experiments measuring cell viability at the indicated phases of the cell cycle in various brain tumor cell lines.

Figure 5A:
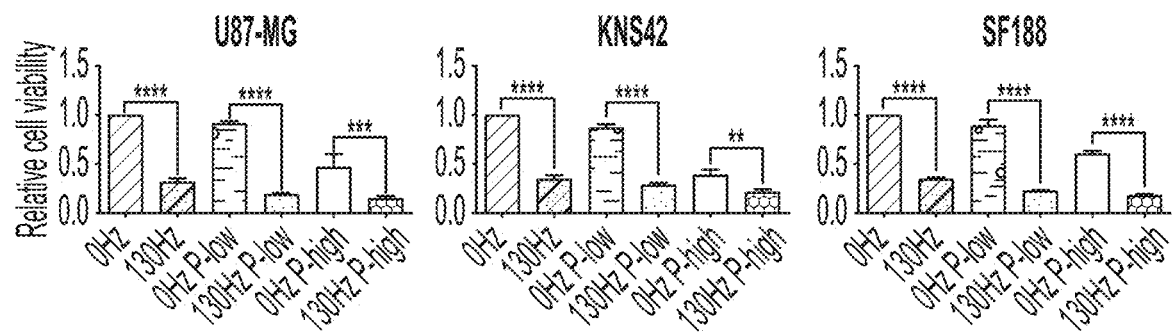
FIG. 5A shows exemplary results of experiments measuring the impact of the combination TTFields with mitotic inhibitor Paclitaxel, in two concentrations, on the viability of brain tumor cell lines.
Figure 5B:
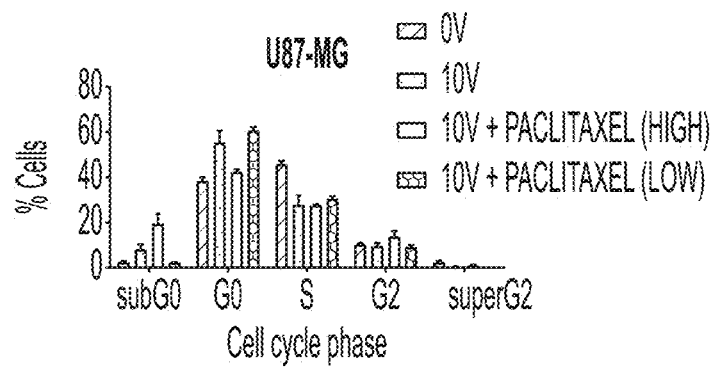
FIG. 5B shows exemplary results of experiments measuring cell viability in brain tumor cell lines at a field strength of 0 V and 10 V in combination at low and high doses of paclitaxel.
Figure 5B:
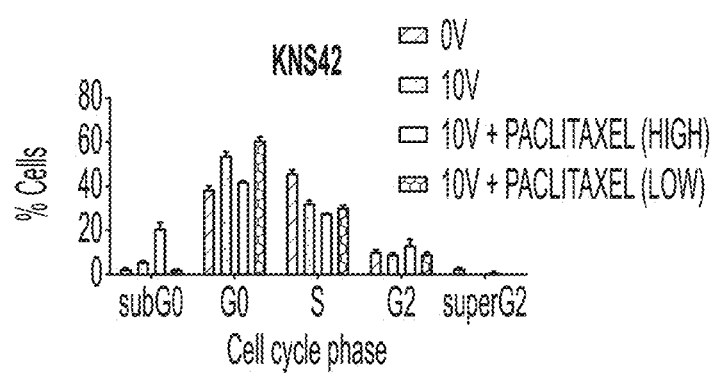
Figure 5B:
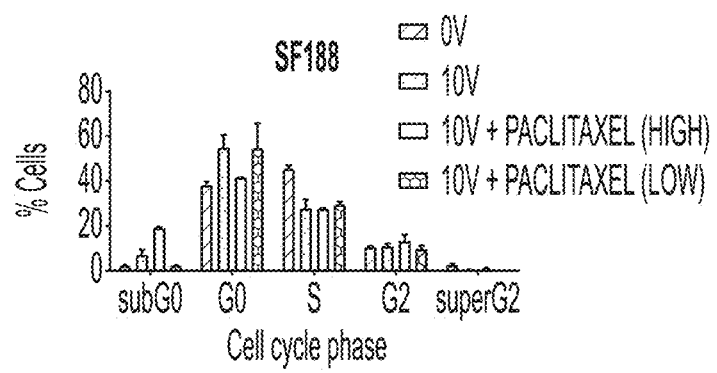

FIG. 5B show the exemplary impact of the combination TTFields with mitotic inhibitors on the viability of brain tumor cell lines. A) SF188, UW228-3, and BXD-1425EPN cell lines were treated for 3 days with TTFields in combination with a higher and lower dose of paclitaxel, with metabolic measurements being taken at the end-point. B) SF188, UW228-3, and BXD-1425EPN cell lines were treated for 3 days with TTFields in combination with a higher and lower dose of mebendazole, with metabolic measurements being taken at the end-point.

Figure 5C:
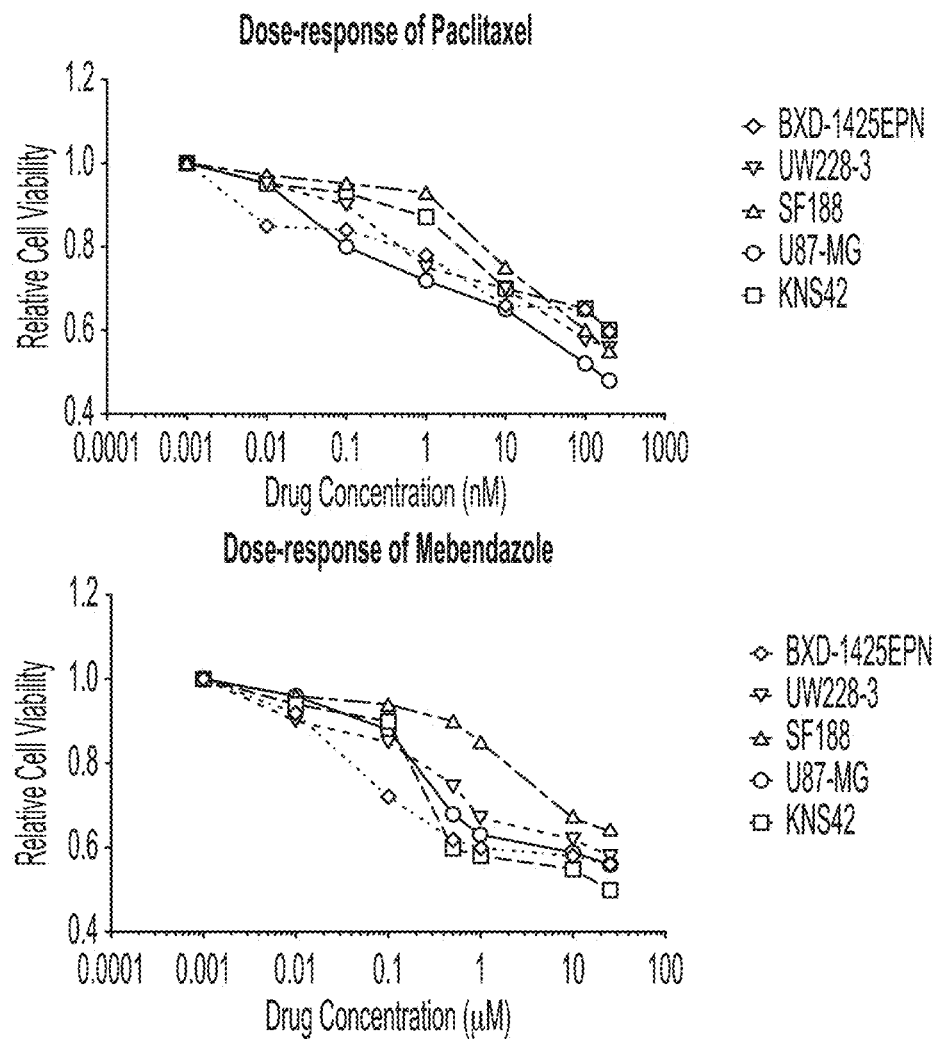
FIG. 5C shows exemplary IC50 curves of TMZ, paclitaxel, and mebendazole for U87-MG, KNS42, SF188, GIN-28, GIN-31, GCE-77, UW228-3, and BXD-1245-EPN cell lines used in the combination experiments.

FIG. 5C provides exemplary IC50 curves of TMZ, paclitaxel, and mebendazole for U87-MG, KNS42, SF188, GIN-28, GIN-31, GCE-77, UW228-3, and BXD-1245-EPN cell lines used in the combination experiments. The curves have the higher and lower doses used in the combinational experiments indicated.

Figure 6:
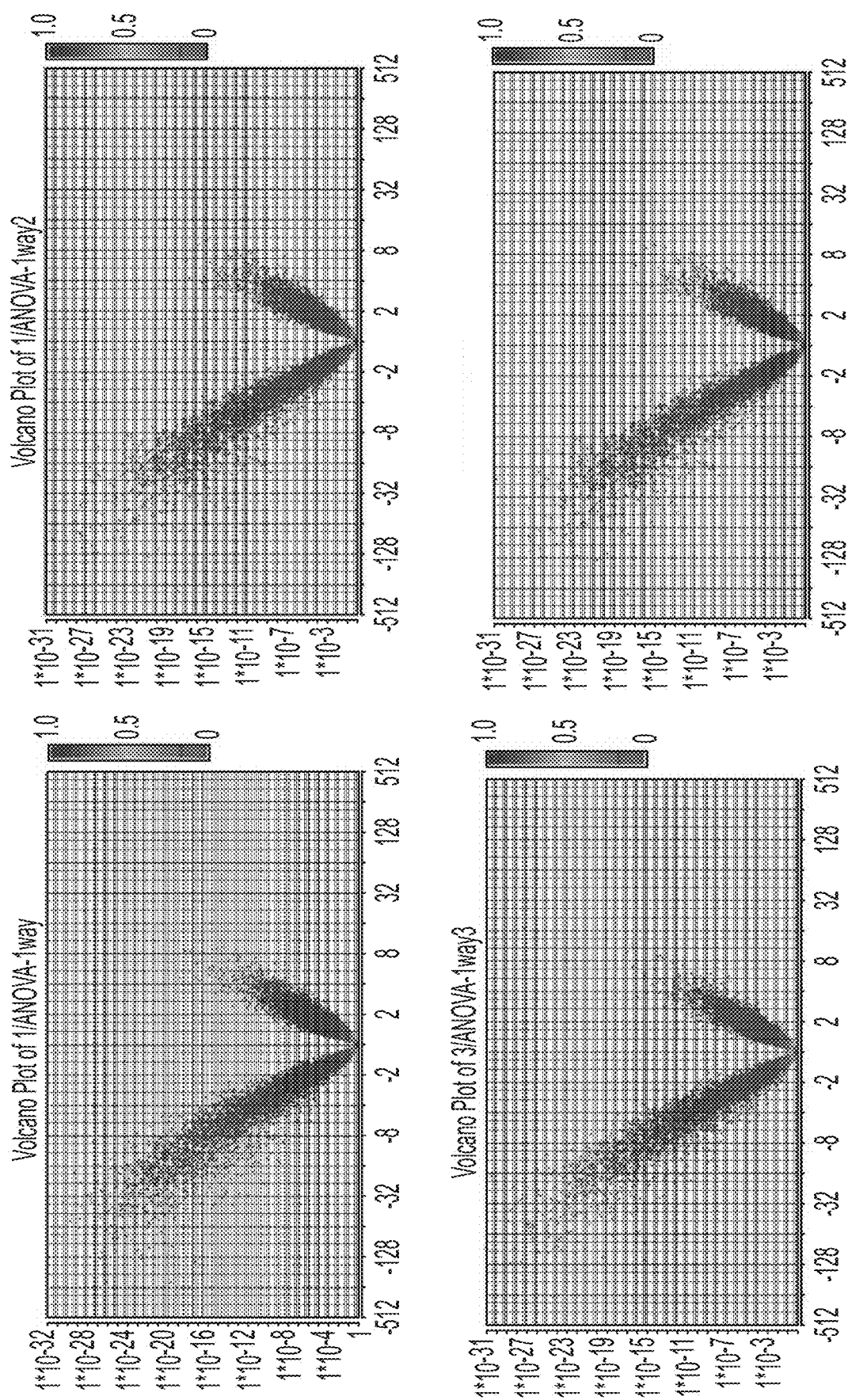
FIG. 6 shows exemplary Volcano plots demonstrating the gene expression patterns of up-regulation and down-regulation of GBM cell lines following treatment with alternating electric fields.

FIG. 6 provides exemplary Volcano plots demonstrating the gene expression patterns of up-regulation and down-regulation of GBM cell lines following electrical treatment. KNS42 and GIN-31 cells treated with 200 kHz TTFields relative to untreated cells.

FIG. 7: Table of top 50 differentially expressed genes from electrically treated cells versus sham controls in GIN-31 and KNS42 cell lines.

Figure 8A:
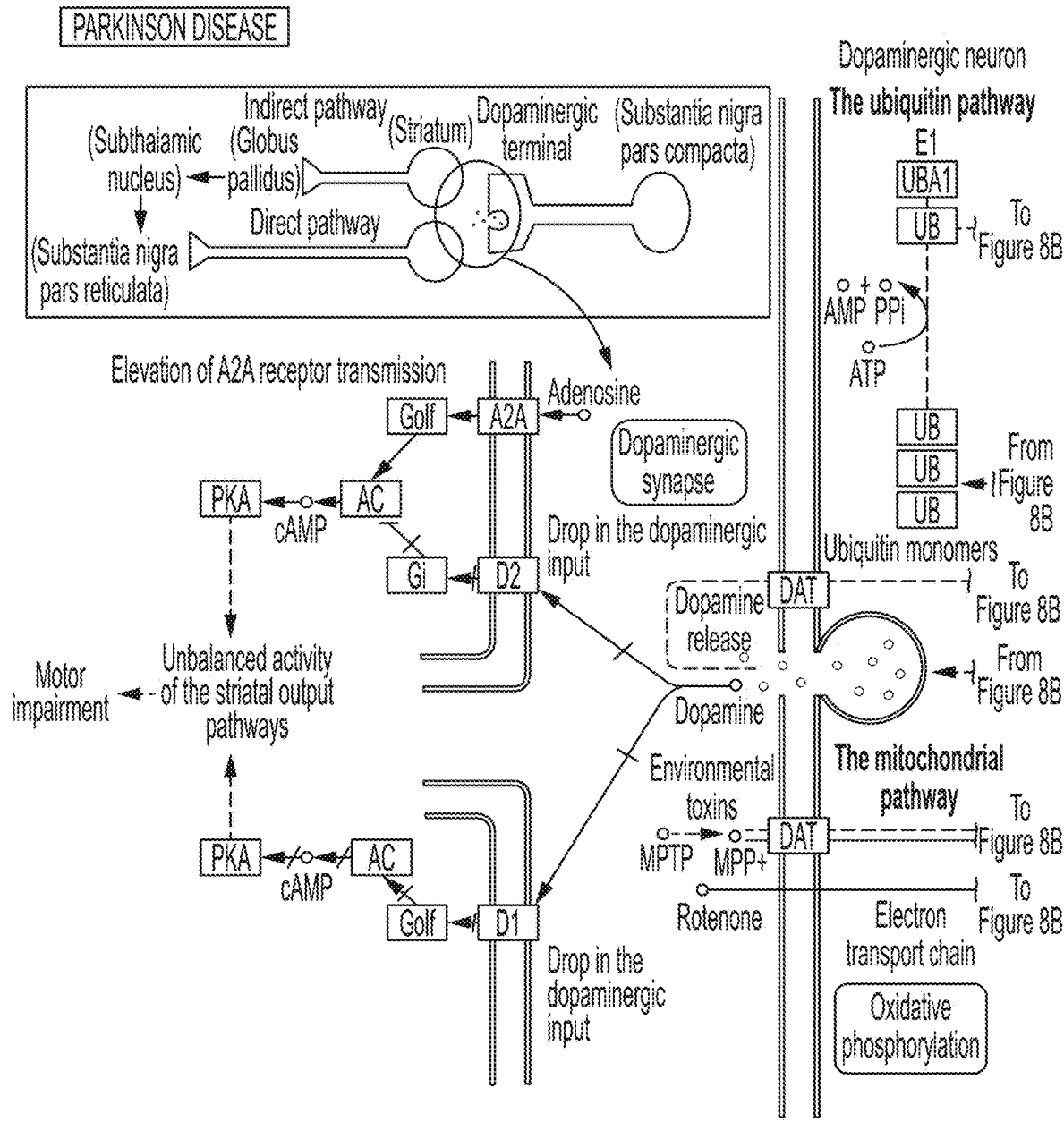
FIGS. 8A-8B illustrate the KEGG Pathway for Parkinson Disease.
Figure 8B:
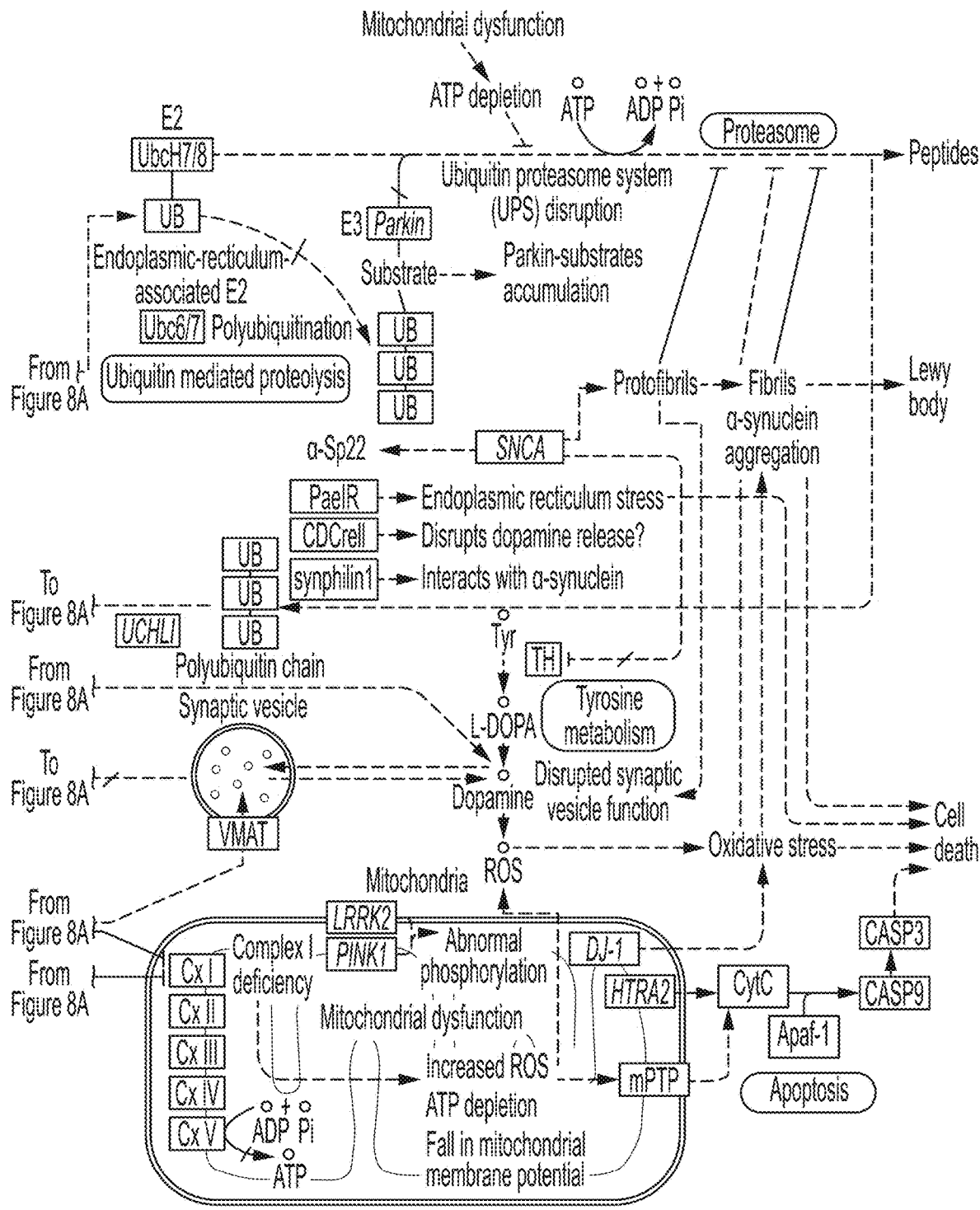
Figure 9A:
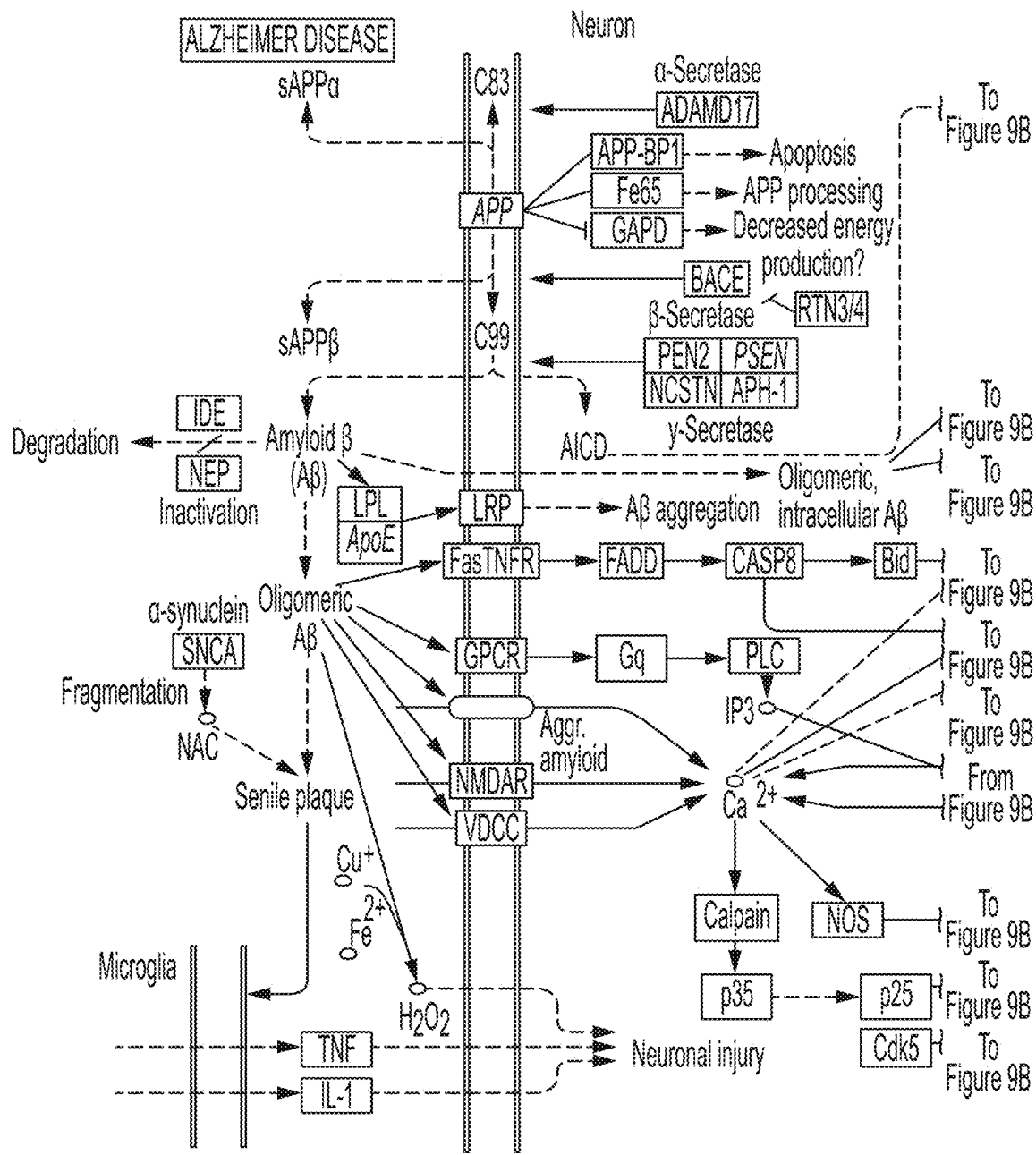
FIGS. 9A-9B illustrate the KEGG Pathway for Alzheimer Disease.
Figure 9B:
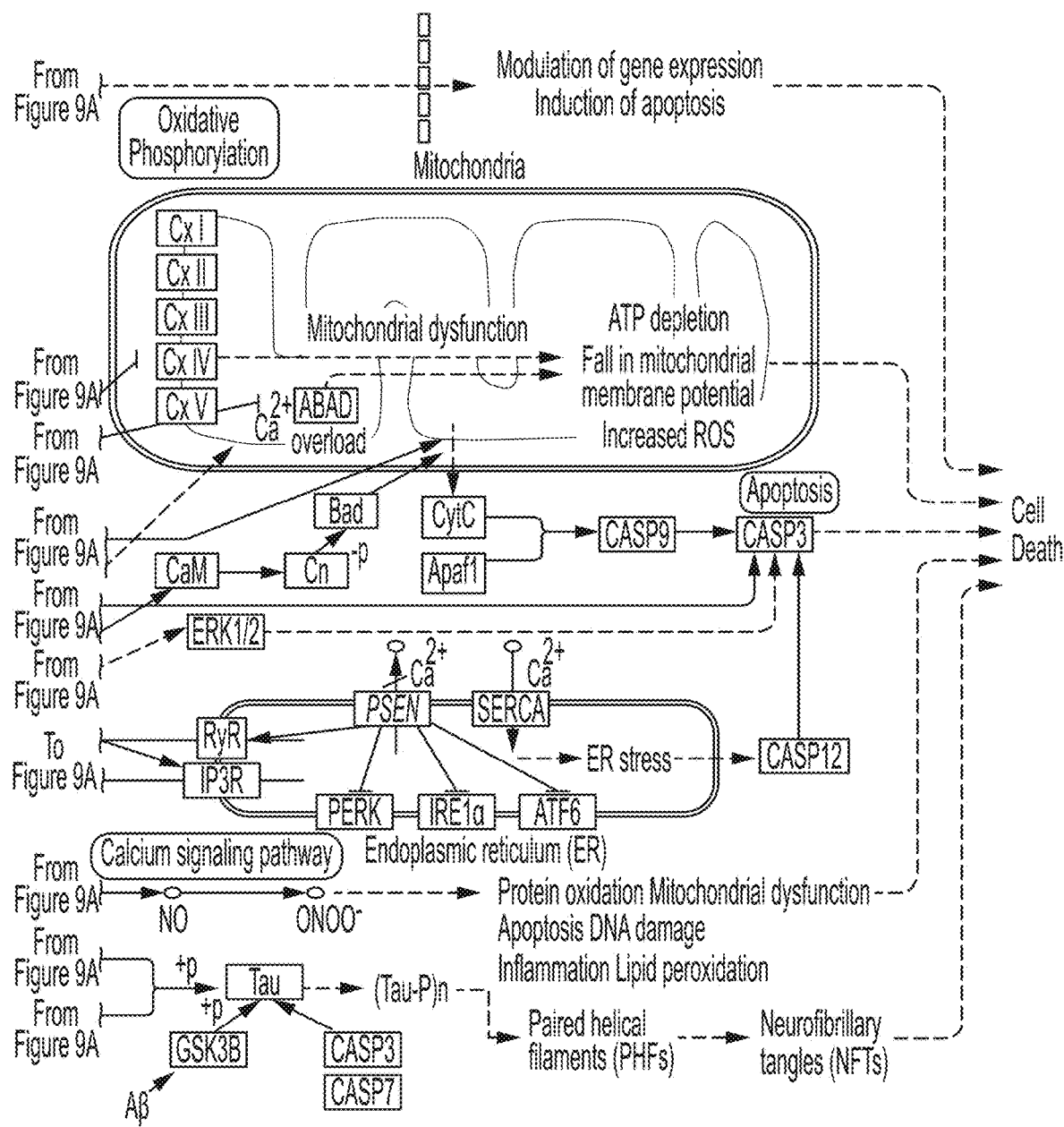

FIGS. 8A-8B illustrate the KEGG Pathway for Parkinson Disease;

FIGS. 9A-9B illustrate the KEGG Pathway for Alzheimer Disease, and

Figure 10A:
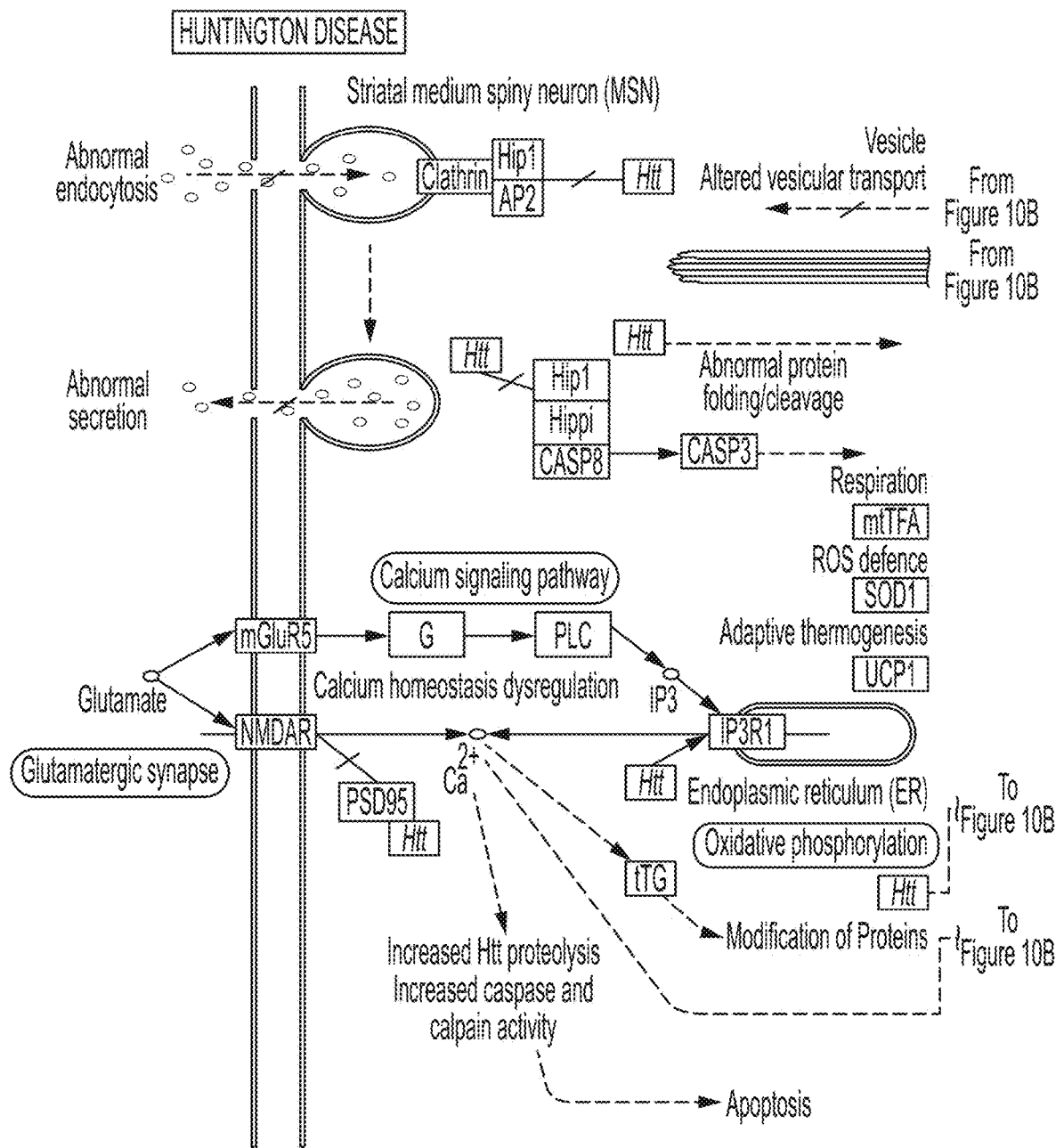
FIGS. 10A-10B illustrate the KEGG Pathway for Huntington Disease.
Figure 10B:
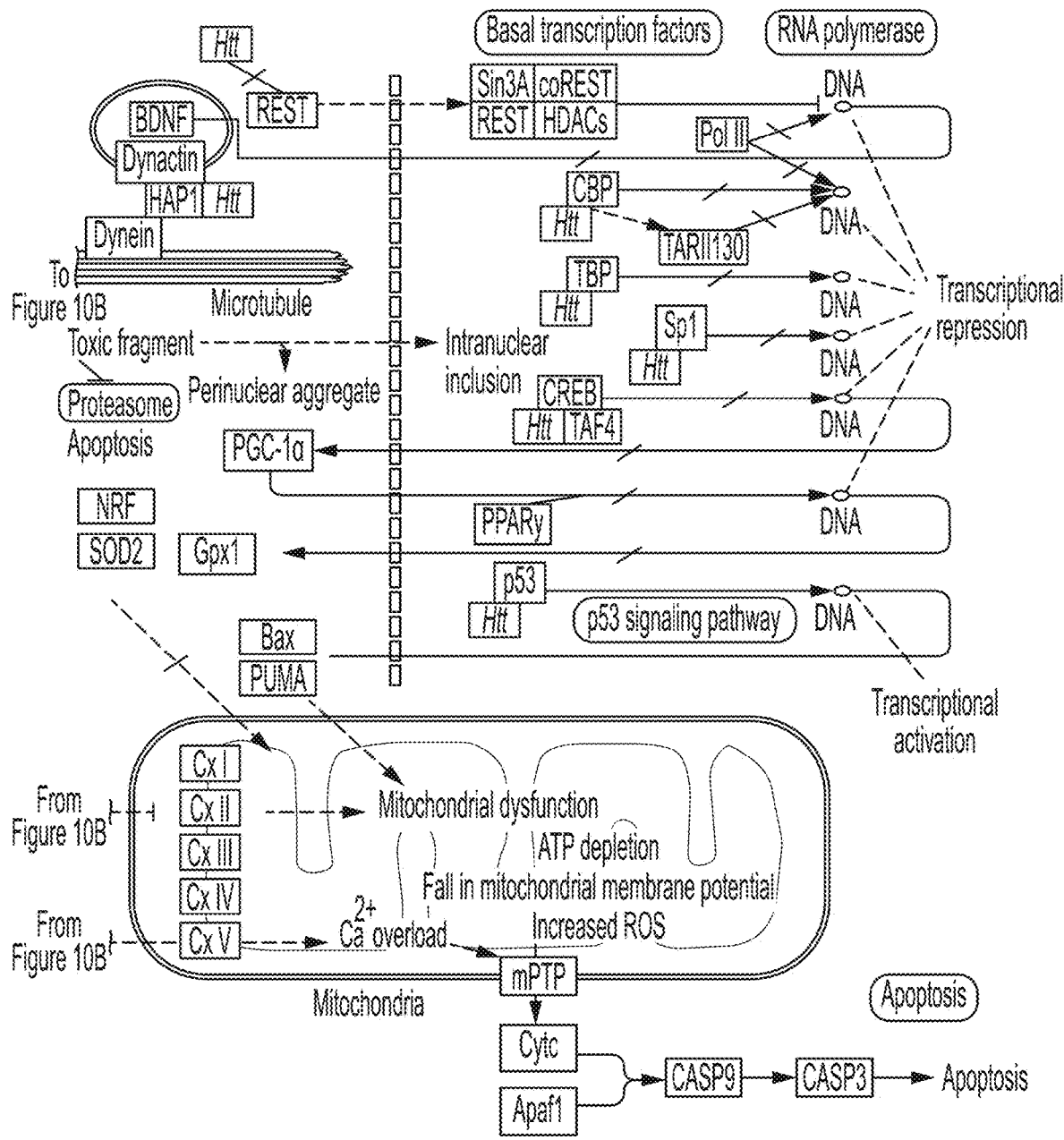

FIGS. 10A-10B illustrate the KEGG Pathway for Huntington Disease.

As shown in FIG. 11A, KNS42 and GIN-31 cell lines were treated for 72 hours at the determined optimal frequency TTFields with the Inovitro and gene expression changes were assessed via Clariom™ S Assay arrays (Significance criteria; FDR <0.05 and fold-change <−2 or >2).

FIG. 11B shows a Western blot of MT-ND5, BTNL9 and GAPDH as the control. Target genes were among the top 50 most significantly differentially expressed genes for both treatments. Western blot validates downregulation of MT-ND5 and CTSB, and the upregulation of BTNL9 following electrical treatment.

REFERENCES

AGNESI, F., JOHNSON, M. D. & VITEK, J. L. 2013. Deep brain stimulation: how does it work? Handb Clin Neurol, 116, 39-54.

BAI, Y., SHAKELEY, R. M. & ATTARDI, G. 2000. Tight control of respiration by NADH dehydrogenase ND5 subunit gene expression in mouse mitochondria. Molecular and cellular biology, 20, 805-815.

BENSON, L. Tumor treating fields technology: alternating electric field therapy for the treatment of solid tumors. Seminars in oncology nursing, 2018. Elsevier, 137-150.

BERNARD-ARNOUX, F., LAMURE, M., DUCRAY, F., AULAGNER, G., HONNORAT, J. & ARMOIRY, X. 2016. The cost-effectiveness of tumor-treating fields therapy in patients with newly diagnosed glioblastoma. Neuro-oncology, 18, 1129-1136.

CHAUDHRY, A., BENSON, L., VARSHAVER, M., FARBER, O., WEINBERG, U., KIRSON, E. & PALTI, Y. 2015. NovoTTF™-100A System (Tumor Treating Fields) transducer array layout planning for glioblastoma: a NovoTAL™ system user study. World J Surg Oncol, 13, 316.

CHEN, E. Y., TAN, C. M., KOU, Y., DUAN, Q., WANG, Z., MEIRELLES, G. V., CLARK, N. R. & MA'AYAN, A. 2013. Enrichr: interactive and collaborative HTML5 gene list enrichment analysis tool. BMC bioinformatics, 14, 128.

CHIKEN, S. & NAMBU, A. 2016. Mechanism of Deep Brain Stimulation: Inhibition, Excitation, or Disruption? Neuroscientist, 22, 313-22.

CLARK, P. A., GAAL, J. T., STREBE, J. K., PASCH, C. A., DEMING, D. A., KUO, J. S. & ROBINS, H. I. 2016. The effects of tumor treating fields and temozolomide in MGMT expressing and non-expressing patient-derived glioblastoma cells. J Clin Neurosci.

CUCULLO, L., DINI, G., HALLENE, K. L., FAZIO, V., ILKANICH, E. V., IGBOECHI, C., KIGHT, K. M., AGARWAL, M. K., GARRITY-MOSES, M. & JANIGRO, D. 2005. Very low intensity alternating current decreases cell proliferation. Glia, 51, 65-72.

GERA, N., YANG, A., HOLTZMAN, T. S., LEE, S. X., WONG, E. T. & SWANSON, K. D. 2015. Tumor treating fields perturb the localization of septins and cause aberrant mitotic exit. PLoS One, 10, e0125269.

GILADI, M., MUNSTER, M., SCHNEIDERMAN, R. S., VOLOSHIN, T., PORAT, Y., BLAT, R., ZIELINSKA-CHOMEJ, K., HÅÅG, P., BOMZON, Z. E. & KIRSON, E. D. 2017. Tumor treating fields (TTFields) delay DNA damage repair following radiation treatment of glioma cells. Radiation Oncology, 12, 206.

GILADI, M., SCHNEIDERMAN, R. S., VOLOSHIN, T., PORAT, Y., MUNSTER, M., BLAT, R., SHERBO, S., BOMZON, Z., URMAN, N., ITZHAKI, A., CAHAL, S., SHTEINGAUZ, A., CHAUDHRY, A., KIRSON, E. D., WEINBERG, U. & PALTI, Y. 2015. Mitotic Spindle Disruption by Alternating Electric Fields Leads to Improper Chromosome Segregation and Mitotic Catastrophe in Cancer Cells. Sci Rep, 5, 18046.

HEGI, M. E., DISERENS, A. C., GORLIA, T., HAMOU, M. F., DE TRIBOLET, N., WELLER, M., KROS, J. M., HAINFELLNER, J. A., MASON, W., MARIANI, L., BROMBERG, J. E., HAU, P., MIRIMANOFF, R. O., CAIRNCROSS, J. G., JANZER, R. C. & STUPP, R. 2005. MGMT gene silencing and benefit from temozolomide in glioblastoma. N Engl J Med, 352, 997-1003.

JANG, M., KIM, S. S. & LEE, J. 2013. Cancer cell metabolism: implications for therapeutic targets. Experimental & molecular medicine, 45, e45.

JO, Y., HWANG, S.-G., JIN, Y. B., SUNG, J., JEONG, Y. K., BAEK, J. H., CHO, J.-M., KIM, E. H. & YOON, M. 2018. Selective toxicity of tumor treating fields to melanoma: an in vitro and in vivo study. Cell death discovery, 5, 46.

JULIA, T., WANG, M., PIMENOVA, A. A., BOWLES, K. R., HARTLEY, B. J., LACIN, E., MACHLOVI, S. I., ABDELAAL, R., KARCH, C. M. & PHATNANI, H. 2017. An efficient platform for astrocyte differentiation from human induced pluripotent stem cells. Stem Cell Reports, 9, 600-614.

KESSLER, A. F., FRÖMBLING, G. E., GROSS, F., HAHN, M., DZOKOU, W., ERNESTUS, R.-I., LÖHR, M. & HAGEMANN, C. 2018. Effects of tumor treating fields (TTFields) on glioblastoma cells are augmented by mitotic checkpoint inhibition. Cell death discovery, 5, 12.

KIRSON, E. D., DBALÝ, V., TOVARYS, F., VYMAZAL, J., SOUSTIEL, J. F., ITZHAKI, A., MORDECHOVICH, D., STEINBERG-SHAPIRA, S., GURVICH, Z., SCHNEIDERMAN, R., WASSERMAN, Y., SALZBERG, M., RYFFEL, B., GOLDSHER, D., DEKEL, E. & PALTI, Y. 2007. Alternating electric fields arrest cell proliferation in animal tumor models and human brain tumors. Proc Natl Acad Sci USA, 104, 10152-7.

KIRSON, E. D., GURVICH, Z., SCHNEIDERMAN, R., DEKEL, E., ITZHAKI, A., WASSERMAN, Y., SCHATZBERGER, R. & PALTI, Y. 2004. Disruption of cancer cell replication by alternating electric fields. Cancer Res, 64, 3288-95.

KIRSON, E. D., SCHNEIDERMAN, R. S., DBALÝ, V., TOVARYS, F., VYMAZAL, J., ITZHAKI, A., MORDECHOVICH, D., GURVICH, Z., SHMUELI, E., GOLDSHER, D., WASSERMAN, Y. & PALTI, Y. 2009. Chemotherapeutic treatment efficacy and sensitivity are increased by adjuvant alternating electric fields (TTFields). BMC Med Phys, 9, 1.

KORSHOEJ, A. R., HANSEN, F. L., MIKIC, N., VON OETTINGEN, G., SØRENSEN, J. C. H. & THIELSCHER, A. 2018. Importance of electrode position for the distribution of tumor treating fields (TTFields) in a human brain. Identification of effective layouts through systematic analysis of array positions for multiple tumor locations. PLoS One, 13, e0201957.

KULESHOV, M. V., JONES, M. R., ROUILLARD, A. D., FERNANDEZ, N. F., DUAN, Q., WANG, Z., KOPLEV, S., JENKINS, S. L., JAGODNIK, K. M. & LACHMANN, A. 2016. Enrichr: a comprehensive gene set enrichment analysis web server 2016 update. Nucleic acids research, 44, W90-W97.

LIN, M. T. & BEAL, M. F. 2006. Mitochondrial dysfunction and oxidative stress in neurodegenerative diseases. Nature, 443, 787.

MUKHTAR, E., ADHAMI, V. M. & MUKHTAR, H. 2014. Targeting microtubules by natural agents for cancer therapy. Molecular cancer therapeutics, 13, 275-284.

NEUHAUS, E., ZIRJACKS, L., GANSER, K., KLUMPP, L., SCHÜLER, U., ZIPS, D., ECKERT, F. & HUBER, S. M. 2019. Alternating Electric Fields (TTFields) Activate Cav1. 2 Channels in Human Glioblastoma Cells. Cancers, 11, 110.

PORAT, Y., GILADI, M., SCHNEIDERMAN, R. S., BLAT, R., SHTEINGAUZ, A., ZEEVI, E., MUNSTER, M., VOLOSHIN, T., KAYNAN, N. & TAL, O. 2017. Determining the Optimal Inhibitory Frequency for Cancerous Cells Using Tumor Treating Fields (TTFields). Journal of visualized experiments: JoVE.

RAPP, M., BAERNREUTHER, J., TUROWSKI, B., STEIGER, H.-J., SABEL, M. & KAMP, M. A. 2017. Recurrence pattern analysis of primary glioblastoma. World neurosurgery, 103, 733-740.

SCHWARTZBAUM, J. A., FISHER, J. L., ALDAPE, K. D. & WRENSCH, M. 2006. Epidemiology and molecular pathology of glioma. Nature Reviews Neurology, 2, 494.

SEBASTIANO, A. R., DEWEYERT, A., BENOIT, S., IREDALE, E., XU, H., OLIVEIRA, C., WONG, E., SCHMID, S. & HEBB, M. O. 2018. Preclinical outcomes of Intratumoral Modulation Therapy for glioblastoma. Scientific reports, 8, 7301.

SHTEINGAUZ, A., PORAT, Y., GILADI, M., SCHNEIDERMAN, R., VOLOSHIN, T., MUNSTER, M., KIRSON, E., WEINBERG, U. & PALTI, Y. 2018. Induction of autophagy following TTFields application serves as a survival mechanism mediated by AMPK activation. AACR.

SILGINER, M., WELLER, M., STUPP, R. & ROTH, P. 2017. Biological activity of tumor-treating fields in preclinical glioma models. Cell Death & Disease, 8, e2753.

STUPP, R., MASON, W. P., VAN DEN BENT, M. J., WELLER, M., FISHER, B., TAPHOORN, M. J., BELANGER, K., BRANDES, A. A., MAROSI, C., BOGDAHN, U., CURSCHMANN, J., JANZER, R. C., LUDWIN, S. K., GORLIA, T., ALLGEIER, A., LACOMBE, D., CAIRNCROSS, J. G., EISENHAUER, E., MIRIMANOFF, R. O., GROUPS, E. O. F. R. A. T. O. C. B. T. A. R. & GROUP, N. C. I. O. C. C. T. 2005. Radiotherapy plus concomitant and adjuvant temozolomide for glioblastoma. N Engl J Med, 352, 987-96.

STUPP, R., TAILLIBERT, S., KANNER, A. & ET AL. 2017. Effect of tumor-treating fields plus maintenance temozolomide vs maintenance temozolomide alone on survival in patients with glioblastoma: A randomized clinical trial. JAMA, 318, 2306-2316.

STUPP, R., WONG, E. T., KANNER, A. A., STEINBERG, D., ENGELHARD, H., HEIDECKE, V., KIRSON, E. D., TAILLIBERT, S., LIEBERMANN, F. & DBALÝ, V. 2012a. NovoTTF-100A versus physician's choice chemotherapy in recurrent glioblastoma: a randomised phase III trial of a novel treatment modality. European journal of cancer, 48, 2192-2202.

STUPP, R., WONG, E. T., KANNER, A. A., STEINBERG, D., ENGELHARD, H., HEIDECKE, V., KIRSON, E. D., TAILLIBERT, S., LIEBERMANN, F., DBALÝ, V., RAM, Z., VILLANO, J. L., RAINOV, N., WEINBERG, U., SCHIFF, D., KUNSCHNER, L., RAIZER, J., HONNORAT, J., SLOAN, A., MALKIN, M., LANDOLFI, J. C., PAYER, F., MEHDORN, M., WEIL, R. J., PANNULLO, S. C., WESTPHAL, M., SMRCKA, M., CHIN, L., KOSTRON, H., HOFER, S., BRUCE, J., COSGROVE, R., PALEOLOGOUS, N., PALTI, Y. & GUTIN, P. H. 2012b. NovoTTF-100A versus physician's choice chemotherapy in recurrent glioblastoma: a randomised phase III trial of a novel treatment modality. Eur J Cancer, 48, 2192-202.

VOLOSHIN, T., MUNSTER, M., BLATT, R., SHTEINGAUZ, A., ROBERTS, P. C., SCHMELZ, E. M., GILADI, M., SCHNEIDERMAN, R. S., ZEEVI, E., PORAT, Y., BOMZON, Z., URMAN, N., ITZHAKI, A., CAHAL, S., KIRSON, E. D., WEINBERG, U. & PALTI, Y. 2016. Alternating electric fields (TTFields) in combination with paclitaxel are therapeutically effective against ovarian cancer cells in vitro and in vivo. Int J Cancer, 139, 2850-2858.

WENGER, C., MIRANDA, P., SALVADOR, R., THIELSCHER, A., BOMZON, Z., GILADI, M., MRUGALA, M. M. & KORSHOEJ, A. R. 2018. A review on Tumor Treating Fields (TTFields): Clinical implications inferred from computational modeling. IEEE Reviews in Biomedical Engineering.

WICK, W. 2016. TTFields: where does all the skepticism come from?: Society for Neuro-Oncology.

XU, H., BIHARI, F., WHITEHEAD, S., WONG, E., SCHMID, S. & HEBB, M. O. 2016. In Vitro Validation of Intratumoral Modulation Therapy for Glioblastoma. Anticancer research, 36, 71-80.

YANG, M. & BRACKENBURY, W. J. 2013. Membrane potential and cancer progression. Frontiers in physiology, 4, 185.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating an autoinflammatory disease in a target region of a subject's body, the method comprising:
    positioning a plurality of electrodes in or on the subject's body, positioned with respect to the target region so that application of an AC voltage between the plurality of electrodes will impose an alternating electric field through tissue that is being affected by the autoinflammatory disease in the target region; and
    applying an AC voltage between the plurality of electrodes for an interval of time, such that an alternating electric field is imposed through the tissue for the interval of time,
    wherein the alternating electric field has a frequency and a field strength such that when the alternating electric field is imposed in the tissue for the interval of time, the alternating electric field inhibits inflammation in the tissue, wherein the alternating electric field has a frequency between 50 and 500 kHz.

2. The method of claim 1, wherein the autoinflammatory disease is Crohn's disease, and wherein the plurality of electrodes is positioned with respect to the subject's body so that the alternating electric field is imposed in the subject's gastrointestinal system.

3. The method of claim 1, wherein the autoinflammatory disease is intestinal inflammation, and wherein the plurality of electrodes is positioned with respect to the subject's body so that the alternating electric field is imposed in the subject's gastrointestinal system.

4. The method of claim 1, wherein the autoinflammatory disease is irritable bowel syndrome, and wherein the plurality of electrodes is positioned with respect to the subject's body so that the alternating electric field is imposed in the subject's gastrointestinal system.

5. The method of claim 1, wherein the autoinflammatory disease is ulcerative colitis, and wherein the plurality of electrodes is positioned with respect to the subject's body so that the alternating electric field is the subject's gastrointestinal system.

6. The method of claim 1, wherein the autoinflammatory disease is Familial Mediterranean Fever, and wherein the plurality of electrodes is positioned with respect to the subject's body so that the alternating electric field is imposed in the subject's abdomen.

7. The method of claim 1, wherein the positioning comprises
positioning a first set of electrodes in or on the subject's body, wherein the first set of electrodes is positioned with respect to the target region so that application of an AC voltage between the electrodes of the first set will impose an alternating electric field with a first orientation through tissue that is being affected by the autoinflammatory disease in the target region, and
positioning a second set of electrodes in or on the subject's body, wherein the second set of electrodes is positioned with respect to the target region so that application of an AC voltage between the electrodes of the second set will impose an alternating electric field with a second orientation through the tissue, wherein the first orientation and the second orientation are different,
wherein the applying comprises repeating, in an alternating sequence, (a) applying a first AC voltage between the electrodes of the first set, such that an alternating electric field with the first orientation is imposed through the tissue and (b) applying a second AC voltage between the electrodes of the second set, such that an alternating electric field with the second orientation is imposed through the tissue,
wherein the alternating electric field with the first orientation has a frequency and a field strength such that when the alternating electric field with the first orientation is imposed in the tissue, the alternating electric field with the first orientation inhibits inflammation in the tissue, and
wherein the alternating electric field with the second orientation has a frequency and a field strength such that when the alternating electric field with the second orientation is imposed in the tissue, the alternating electric field with the second orientation inhibits inflammation in the tissue.

8. The method of claim 7, wherein the first orientation is offset from the second orientation by at least 60°.

9. The method of claim 1, further comprising treating the autoinflammatory disease with a therapeutically effective drug regimen.

10. The method of claim 1, wherein the tissue is tumor-free.

11. The method of claim 1, wherein the tissue is located in an organ selected from the group consisting of heart, pancreas, liver, lung, kidney, brain, and intestine.

12. The method of claim 1, wherein a level of butyrophilin protein in cells of the tissue is increased by at least 2-fold compared to cells of a tissue that is not exposed to the alternating electric fields.

13. The method of claim 12, wherein the butyrophilin protein is encoded by BTNL9.

14. The method of claim 1, wherein the interval of time is at least 72 hours.

15. A method of treating damage from a mitochondrial disorder in a target region of a subject's body, the method comprising:
positioning a plurality of electrodes in or on the subject's body, positioned with respect to the target region so that application of an AC voltage between the plurality of electrodes will impose an alternating electric field through tissue that is being affected by the mitochondrial disorder in the target region; and
applying an AC voltage between the plurality of electrodes for an interval of time, such that an alternating electric field is imposed through the tissue for the interval of time,
wherein the alternating electric field has a frequency and a field strength such that when the alternating electric field is imposed in the tissue for the interval of time, the alternating electric field treats the mitochondrial disorder in the tissue, wherein the alternating electric field has a frequency between 50 and 500 kHz.

16. The method of claim 15, wherein the mitochondrial disorder is Nonalcoholic fatty liver disease, and wherein the plurality of electrodes is positioned with respect to the subject's body so that the alternating electric field is imposed in the subject's liver.

17. The method of claim 15, wherein a level of MT-ND5 protein in cells of the tissue is reduced by at least 2-fold compared to cells of a tissue that is not exposed to the alternating electric fields.

18. The method of claim 15, wherein the positioning comprises
positioning a first set of electrodes in or on the subject's body, wherein the first set of electrodes is positioned with respect to a target region so that application of an AC voltage between the electrodes of the first set will impose an alternating electric field with a first orientation through a tissue that is being affected by the mitochondrial disorder in the target region, and
positioning a second set of electrodes in or on the subject's body, wherein the second set of electrodes is positioned with respect to the target region so that application of an AC voltage between the electrodes of the second set will impose an alternating electric field with a second orientation through the tissue, wherein the first orientation and the second orientation are different,
wherein the applying comprises repeating, in an alternating sequence, (a) applying a first AC voltage between the electrodes of the first set, such that an alternating electric field with the first orientation is imposed through the tissue and (b) applying a second AC voltage between the electrodes of the second set, such that an alternating electric field with the second orientation is imposed through the tissue, wherein the alternating electric field with the first orientation has a frequency and a field strength such that when the alternating electric field with the first orientation is imposed in the tissue, the alternating electric field with the first orientation treats the mitochondrial disorder in the tissue, and wherein the alternating electric field with the second orientation has a frequency and a field strength such that when the alternating electric field with the second orientation is imposed in the tissue, the alternating electric field with the second orientation treats the mitochondrial disorder in the tissue.

19. The method of claim 18, wherein the first orientation is offset from the second orientation by at least 60°.

20. The method of claim 18, further comprising treating the mitochondrial disorder with a therapeutically effective drug regimen.

21. The method of claim 18, wherein the alternating electric field has a frequency between 50 and 500 kHz.

22. The method of claim 18, wherein the tissue is tumor-free.

23. The method of claim 18, wherein a level of MT-ND5 protein in cells of the tissue is reduced by at least 2-fold compared to cells of a tissue that is not exposed to the alternating electric fields.

* * * * *